US011268119B2

United States Patent
Mitchelson et al.

(10) Patent No.: US 11,268,119 B2
(45) Date of Patent: Mar. 8, 2022

(54) COPPER SUPPLEMENTATION FOR CONTROL OF GLYCOSYLATION IN MAMMALIAN CELL CULTURE PROCESS

(71) Applicant: Biogen MA Inc., Cambridge, MA (US)

(72) Inventors: Fernie Mitchelson, Morrisville, NC (US); Erik Heller Hughes, Raleigh, NC (US); Jessica Mondia, Medford, MA (US); Robin Parish Hyde-Deruyscher, Chapel Hill, NC (US)

(73) Assignee: Biogen MA Inc., Cambridge, MA (US)

( * ) Notice: Subject to any disclaimer, the term of this patent is extended or adjusted under 35 U.S.C. 154(b) by 128 days.

(21) Appl. No.: 15/519,731

(22) PCT Filed: Oct. 16, 2015

(86) PCT No.: PCT/US2015/055856
§ 371 (c)(1),
(2) Date: Apr. 17, 2017

(87) PCT Pub. No.: WO2016/061424
PCT Pub. Date: Apr. 21, 2016

(65) Prior Publication Data
US 2017/0327861 A1     Nov. 16, 2017

Related U.S. Application Data

(60) Provisional application No. 62/065,454, filed on Oct. 17, 2014.

(51) Int. Cl.
*C12P 21/00* (2006.01)
*C12N 5/00* (2006.01)
*C07K 16/28* (2006.01)

(52) U.S. Cl.
CPC ........ *C12P 21/005* (2013.01); *C07K 16/2839* (2013.01); *C12N 5/0018* (2013.01);
(Continued)

(58) Field of Classification Search
CPC .......... C07K 16/00; C07K 16/28; C12P 21/00
See application file for complete search history.

(56) References Cited

U.S. PATENT DOCUMENTS

2012/0034674 A1*  2/2012  Grillberger .......... C07K 14/755
                                                     435/226
2012/0276631 A1   11/2012  Bengea et al.
2014/0271622 A1    9/2014  Prentice

FOREIGN PATENT DOCUMENTS

WO   2012/006591   1/2012
WO   2015/026846   2/2015

OTHER PUBLICATIONS

WHO (Guidelines on Evaluation of Similar Biotheraputic Products (SBPs), 2009, World Health Organization, Geneva Switzerland ) (Year: 2009).*

(Continued)

*Primary Examiner* — Robert J Yamasaki
*Assistant Examiner* — Charles Zoltan Constantine
(74) *Attorney, Agent, or Firm* — Wolf, Greenfield & Sacks, P.C.

(57) ABSTRACT

The present invention pertains to a cell culture medium comprising copper as a media supplement, which was shown to control recombinant protein glycosylation and methods of using thereof. The present invention further pertains to a method of controlling or manipulating glycosylation of a recombinant protein of interest in a large scale cell culture.

11 Claims, 18 Drawing Sheets

Figure 1:
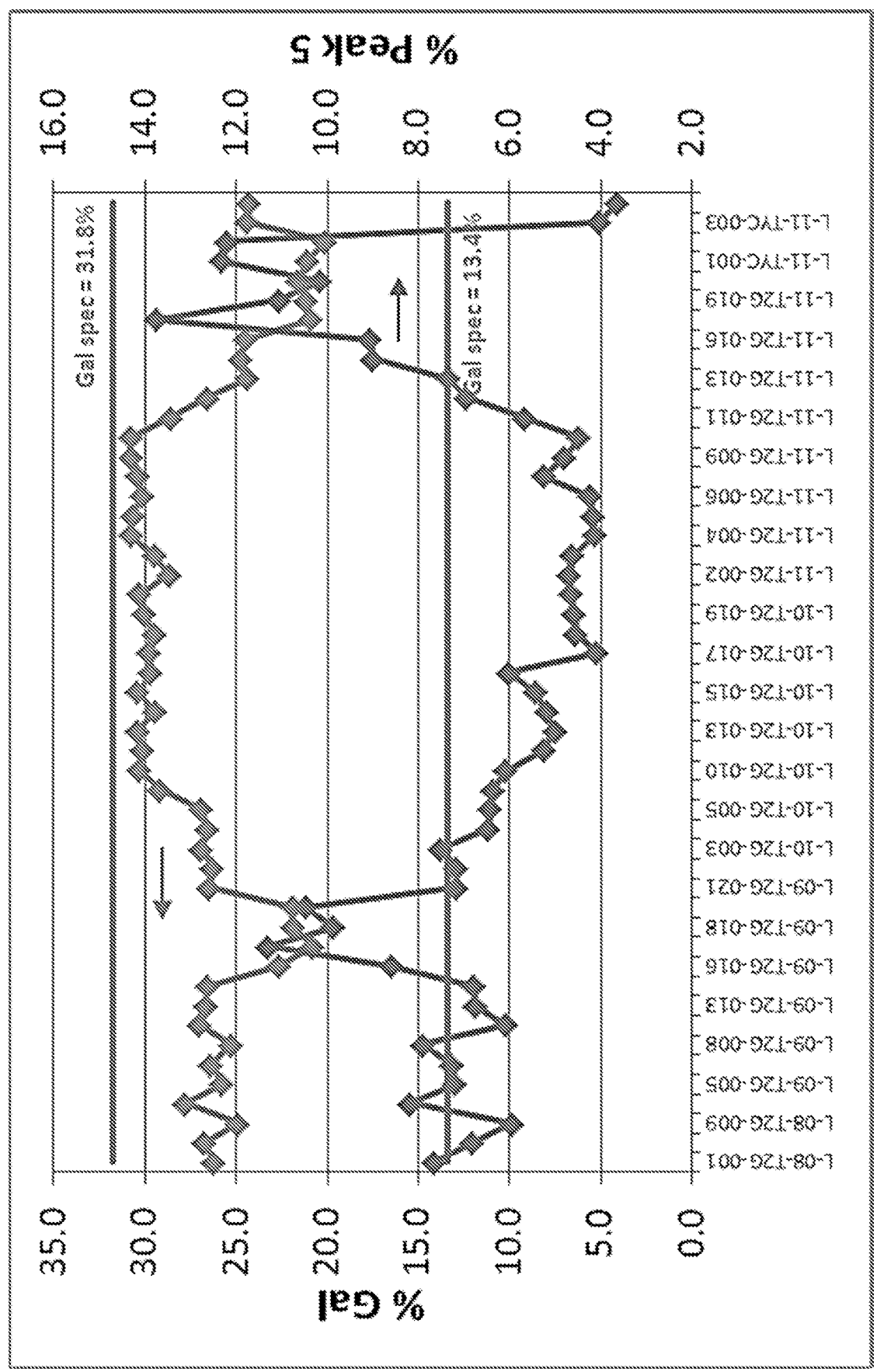

(52) U.S. Cl.
CPC ...... *C07K 2317/14* (2013.01); *C07K 2317/40* (2013.01); *C07K 2317/41* (2013.01); *C12N 2500/10* (2013.01); *C12N 2500/20* (2013.01); *C12N 2511/00* (2013.01); *C12N 2513/00* (2013.01)

(56) References Cited

OTHER PUBLICATIONS

Giorgetti ("Monoclonal antibody N-glycosylation profiling using capillary electrophoresis-Mass spectrometry: Assessment and method validation", Taianta, 178, 2018, 530-537). (Year: 2018).*
International Search Report and Written Opinion for Application No. PCT/US2015/055856 dated Jan. 14, 2016.
International Preliminary Report on Patentability for Application No. PCT/US2015/055856 dated Apr. 27, 2017.

* cited by examiner

A

B

C

D

COPPER SUPPLEMENTATION FOR CONTROL OF GLYCOSYLATION IN MAMMALIAN CELL CULTURE PROCESS

BACKGROUND OF THE INVENTION

Field of the Invention

The present invention pertains to a cell culture medium comprising copper as a media supplement that was shown to control recombinant protein glycosylation and methods of using thereof. The present invention further pertains to a method of controlling or manipulating glycosylation of a recombinant protein of interest in a large scale cell culture, comprising controlling or manipulating the concentration of copper in the cell culture medium.

Background Art

Over the last few decades, much research has focused on the production of therapeutic recombinant proteins, e.g., monoclonal antibodies. While media containing sera or hydrolysates has been utilized, chemically defined media were also developed in order to eliminate the problematic lot-to-lot variation of complex components (Luo and Chen, *Biotechnology and Bioengineering* 97(6):1654-1659 (2007)). An improved understanding of cell culture has permitted a shift to chemically defined medium without compromising growth, viability, titer, etc. To date optimized chemically defined processes have been reported with titers as high as 7.5-10 g/L (Huang et al., *Biotechnology Progress* 26(5):1400-1410 (2010); Ma et al., *Biotechnology Progress* 25(5):1353-1363 (2009); Yu et al., *Biotechnology and Bioengineering* 108(5):1078-1088 (2011)). In general, the high titer chemically defined processes are fed batch processes with cultivation times of 11-18 days. The process intensification has been achieved without compromising product quality while maintaining relatively high viabilities.

Achievement of a robust, scalable production process includes more than increasing the product titer while maintaining high product quality. The process must also predictably require the main carbohydrate source remain constant, such that the feeding strategy does not need to change across scales. As many processes use glucose as the main carbohydrate, and have lactate and ammonium as the main byproducts, the time course of these three critical chemicals should also scale.

A number of reports have demonstrated mammalian host cell-specific processing of N-glycans associated with recombinant proteins (James et al., *Bio/Technology,* 13:592-596 (1995); Lifely et al., *Glycobiology,* 5:813-822 (1995)). These differences may be important for therapeutic proteins as they can directly alter the antigenicity, rate of clearance in vivo, and stability of recombinant proteins (Jenkins et al., *Nature Biotechnol.* 14:975-981 (1996)). Thus, it is important not only to be able to characterize glycans bound to a therapeutic recombinant protein to predict the consequences for in vivo safety and efficacy, but also to understand the cellular controls underpinning glycan processing in a potential host cell enabling the implementation of appropriate strategies to control cellular glycosylation (Grabenhosrt et al., *Glycoconjug. J.,* 16:81-97 (1999); James and Baker, Encyclopedia of bioprocess technology: Fermentation, biocatalysis and bioseparation. New York: John Wiley & Sons. p. 1336-1349 (1999)).

Thus, there is a need in the art for identification of methods that can predictably control glycosylation of proteins of interest.

BRIEF SUMMARY OF THE INVENTION

In one aspect, the present invention is directed to a method for achieving a predetermined galactosylation profile of an anti-α4-integrin antibody comprising adjusting the concentration of copper in a cell culture to achieve a target copper concentration range, wherein the cell culture comprises host cells producing the anti-α4-integrin antibody.

In another aspect, the invention is directed to a method for achieving a predetermined galactosylation profile of an anti-α4-integrin antibody comprising (i) determining a copper concentration in a component of a cell culture medium, (ii) if the copper concentration is below a target copper concentration range, supplementing the component of the cell culture medium with copper to achieve a copper concentration within the target copper concentration range, (iii) producing a cell culture medium using the component of cell culture medium with the target copper concentration, and (iv) culturing a recombinant host cell producing an anti-α4-integrin antibody in the cell culture medium comprising the cell culture medium component.

In another aspect, the invention is directed to a method for achieving a predetermined galactosylation profile of an anti-α4-integrin antibody comprising (i) determining a copper concentration in a component of a cell culture medium, (ii) if the copper concentration is below a target copper concentration range, adding copper to the component of the cell culture medium to achieve a copper concentration within the target copper concentration range, (iii) producing a cell culture medium using the component of cell culture medium with the target copper concentration, and (iv) culturing a recombinant host cell producing an anti-α4-integrin antibody in the cell culture medium comprising the cell culture medium component with the target copper concentration.

In another aspect, the invention is directed to a method for optimizing a cell culture medium for the production of an anti-α4-integrin antibody comprising (i) determining the amount of copper in a cell culture medium or a component used to produce a cell culture medium, and (ii) if the amount of copper is below a target range, supplementing the cell culture medium or the component of the cell culture medium with copper to achieve an amount of copper within the target range, wherein the target range is sufficient to produce anti-α4-integrin antibodies with a predetermined galactosylation profile.

In another aspect, the invention is directed to a method for obtaining a component for a cell culture medium comprising (i) measuring the amount of copper in a hydrolysate from yeast and (ii) if the amount of copper is below a target range, supplementing the yeast hydrolysate with copper to achieve an amount of copper within the target range. In one embodiment, the method comprises supplementing the cell culture with copper if the copper concentration in the cell culture is below the target copper concentration range. In another embodiment, the copper used to supplement the cell culture, cell culture medium component, or hydrolysate from yeast is copper (II) sulfate.

In one embodiment, the predetermined galactosylation profile of the anti-α4-integrin antibodies comprises 13 to 32% galactosylation. In a further embodiment, the predetermined galactosylation profile of the anti-α4-integrin antibody comprises 13.4 to 31.8% galactosylation. In a further embodiment, the predetermined galactosylation profile of the anti-α4-integrin antibody comprises 15 to 31% galactosylation. In a further embodiment, the predetermined galactosylation profile of the anti-α4-integrin antibody comprises 25% galactosylation.

In one embodiment, the target copper concentration range in the cell culture is 1 ppm to 2.4 ppm. In another embodiment, the target copper concentration range in the cell culture is at day 0 between 20 nM and 50 nM and at day 11 between 200 nM and 500 nM. In another embodiment, the target copper concentration is maintained through a feedback loop. In another embodiment, the copper concentration is constantly monitored and maintained within the target copper concentration range. In another embodiment, the target copper concentration is achieved with a single dose of copper.

In one embodiment, the component of the cell culture medium is a yeast hydrolysate. In a preferred embodiment, the hydrolysate is yeastolate.

In another embodiment, the anti-α4-integrin antibodies produced by recombinant host cells cultured in cell culture medium comprising the yeast lysate comprise a predetermined galactosylation profile. In one embodiment, the anti-α4-integrin antibody is produced by a eukaryotic host cell. In a preferred embodiment, the eukaryotic host cell is a mammalian host cell.

In one embodiment, the anti-α4-integrin antibody is produced at a manufacturing scale. In another embodiment, the copper concentration alters the levels of the isoform variants of the anti-α4-integrin antibody. In one embodiment, the anti-α4-integrin antibody is natalizumab.

BRIEF DESCRIPTION OF THE DRAWINGS/FIGURES

FIG. 1. In the absence of copper, significant shifts in galactosylation and pI isoforms were identified among natalizumab product quality characteristics. Peak 5, which represents a single C-terminal lysine residue was specifically noted to shift significantly. Galactosylation (Gal) approached its upper specification. FIG. 1 shows the % Gal and % Peak 5 levels of various large scale manufacturing (LSM) batches.

Figure 2:
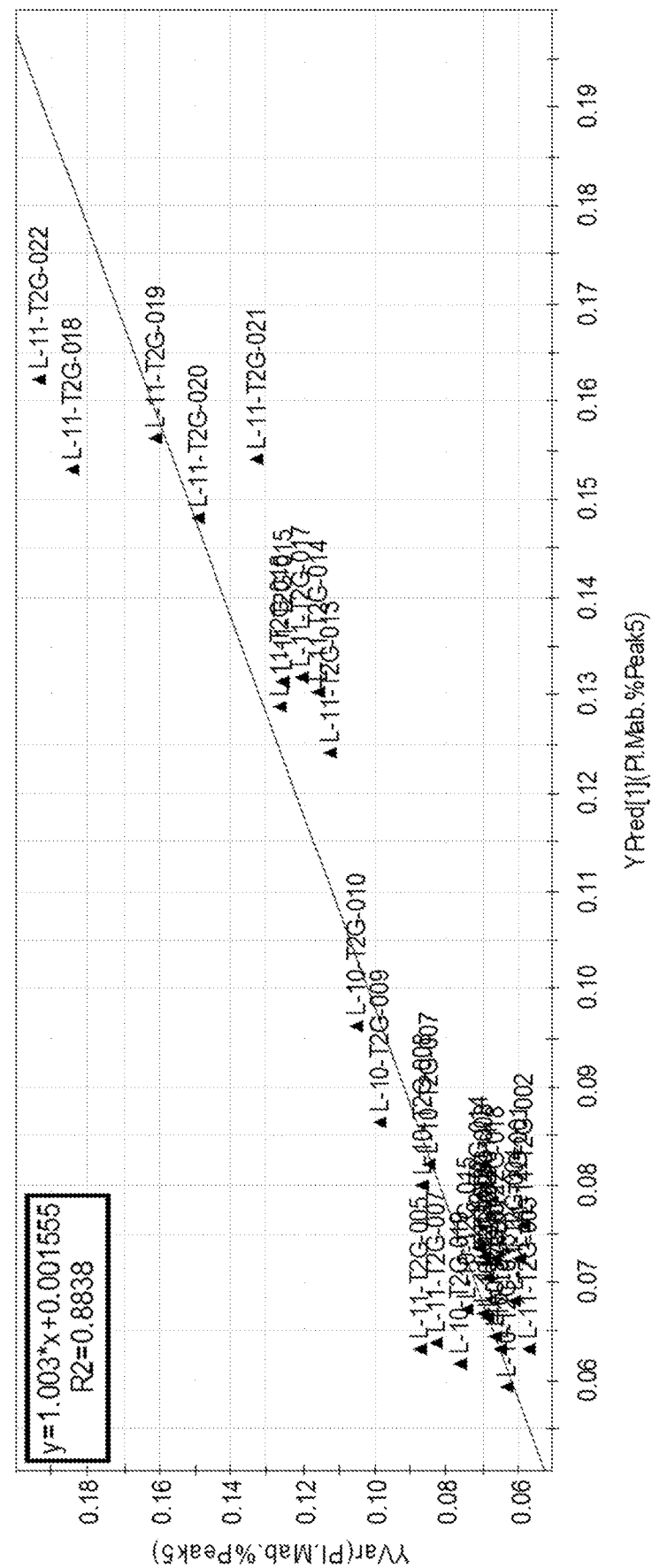
Figure 3:
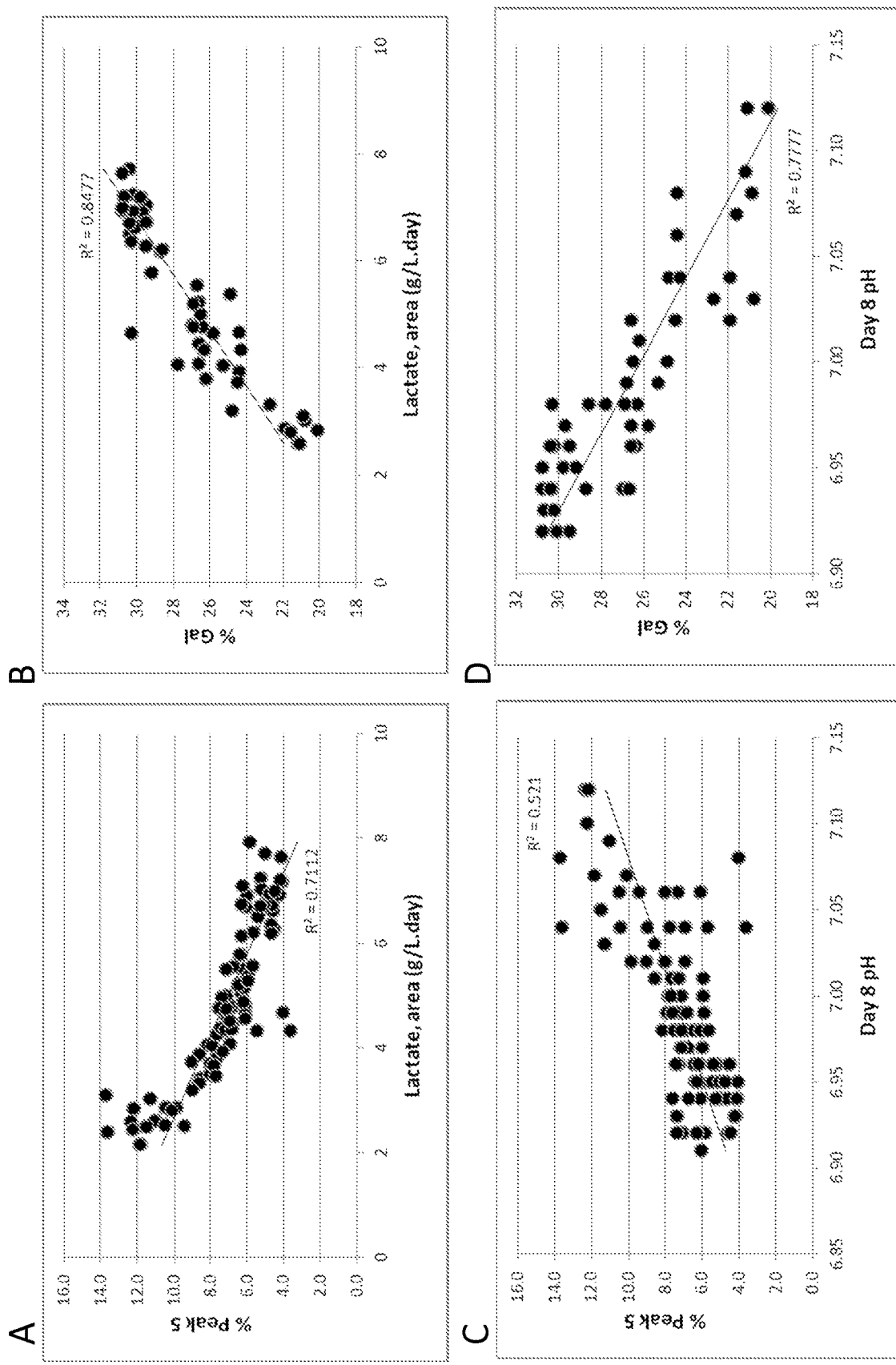

FIG. 2. Comparison of observed versus predicted values for MAb pool peak isoforms from MFM-133-12-R060.

FIGS. 3A-3D. % Peak 5 was plotted against lactate production on Day 8 (3A). % Gal was plotted against lactate production on Day 8 (3B). % Peak 5 was plotted against Day 8 pH (3C). % Gal was plotted against Day 8 pH (3D).

Figure 4:
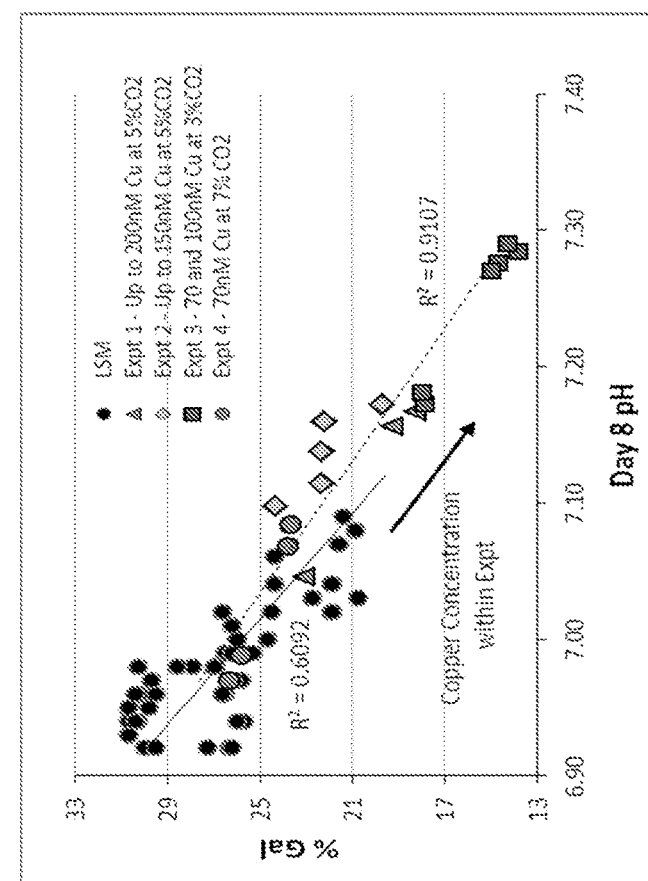
Figure 4:
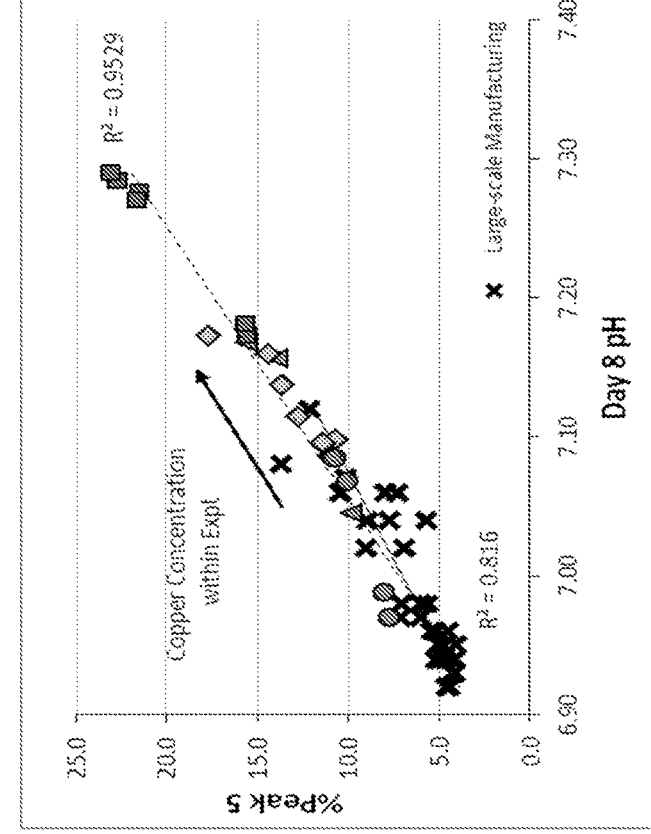
Figure 5:
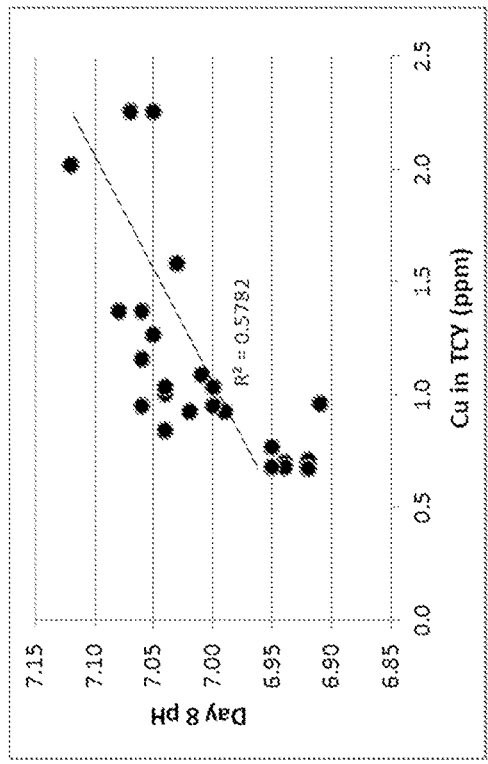
Figure 5:
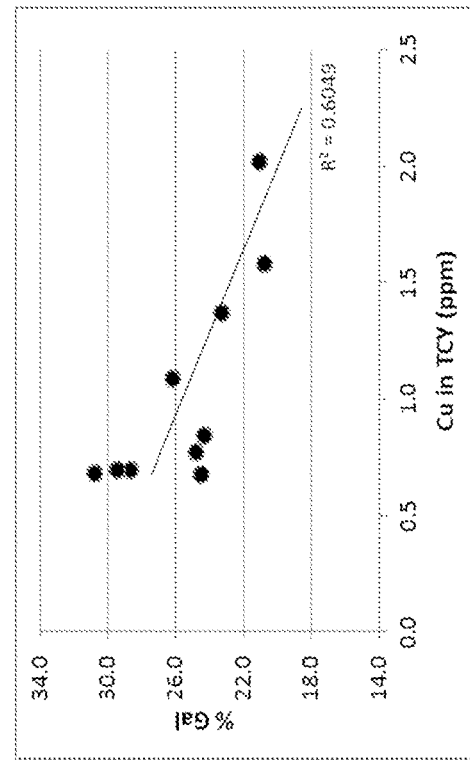
Figure 5:
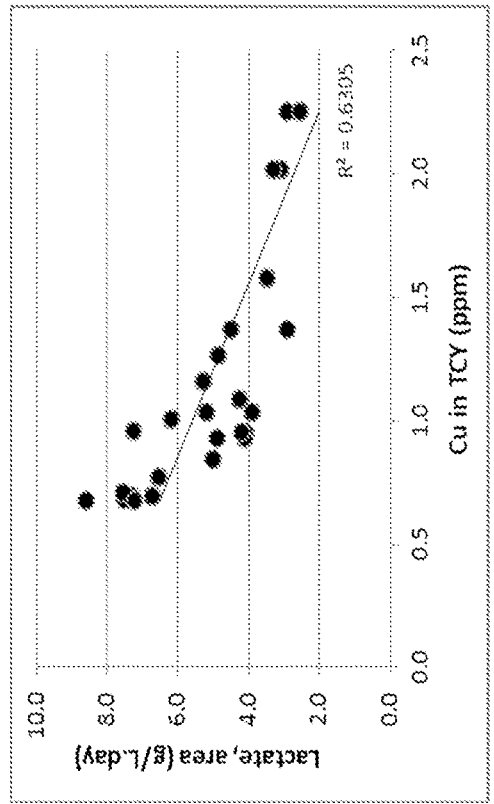
Figure 5:
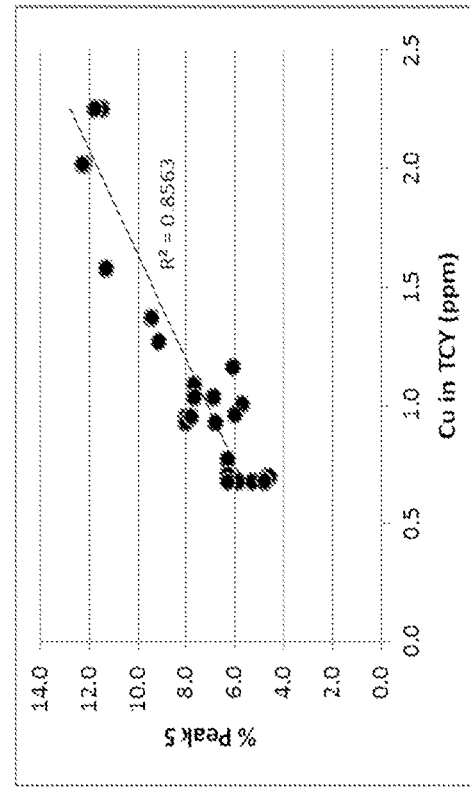

FIGS. 4A-4B. Impact of copper concentration on Peak 5 levels versus Day 8 pH (4A). Impact of copper concentration on Gal levels versus Day 8 pH. Experiments were all conducted in shake flasks and overlaid on large scale manufacturing (LSM) data. Experiment 1 includes up to 200 nM of copper at 5% $CO_2$ in the culture. Experiment 2 includes up to 150 nM of copper at 5% $CO_2$ in the culture. Experiment 3 includes between 70 and 100 nM of copper at 3% $CO_2$ in the culture. Experiment 4 includes 70 nM of copper at 7% $CO_2$ in the culture.

FIGS. 5A-5D. Correlation between lactate levels and copper in TC yeastolate of large scale manufacturing (LSM) batches (5A). Correlation between Day 8 pH and copper in TC yeastolate of LSM batches (5B). Correlation between Peak 5 levels and copper in TC yeastolate of LSM batches (5C). Correlation between Gal levels and copper in TC yeastolate of LSM batches (5D).

Figure 6:
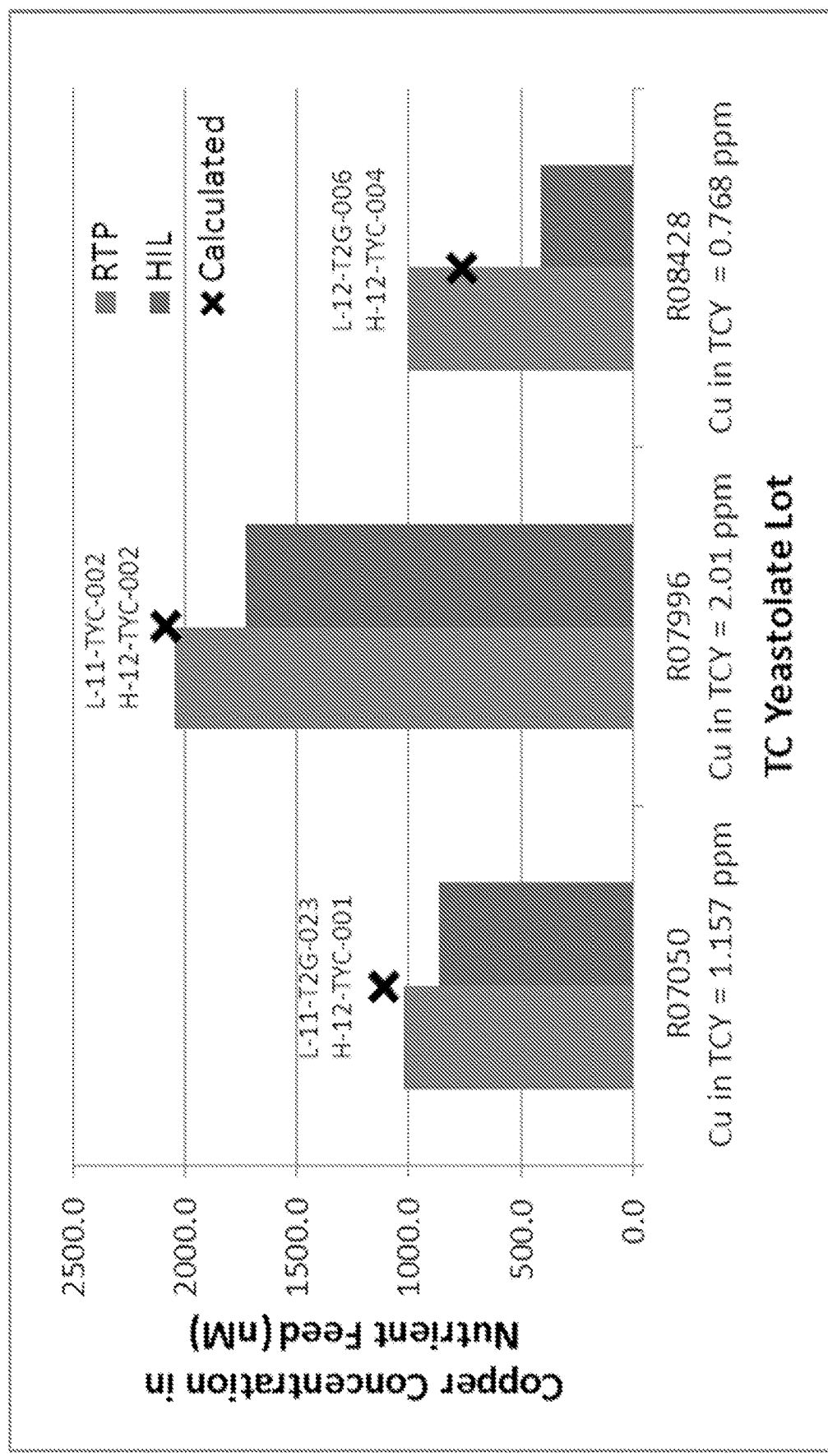

FIG. 6. Copper concentrations were measured in Facility A and B nutrient feeds using the same TC yeastolate lot.

Figure 7:
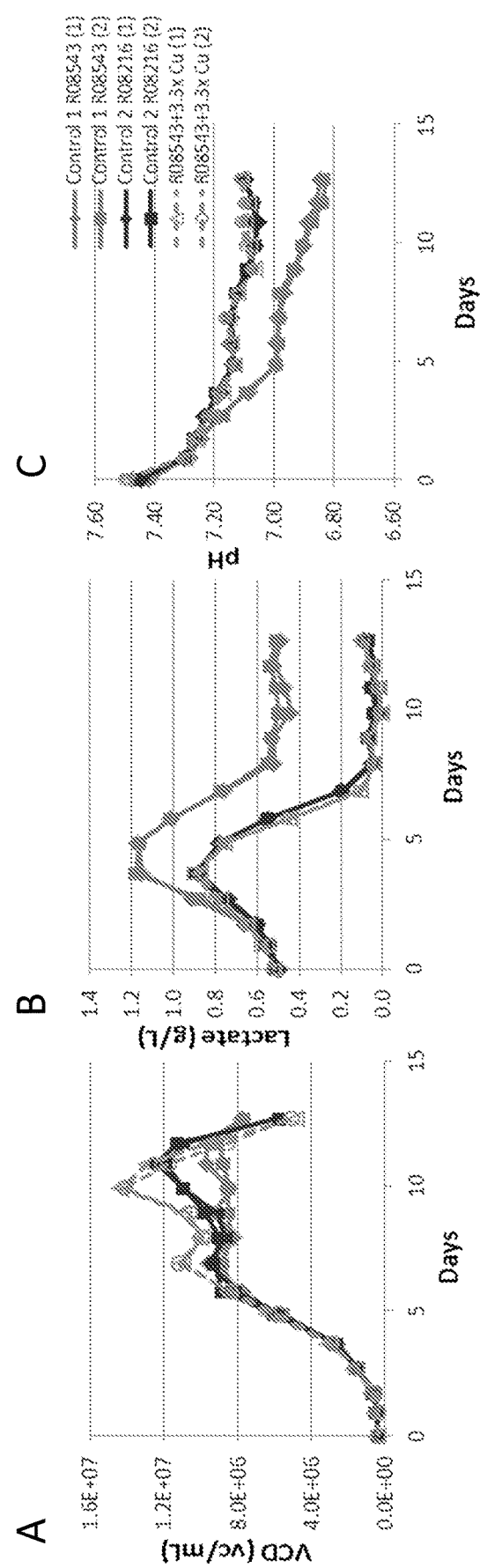

FIGS. 7A-7C. VCD profile of production shake flask cultures using TC yeastolate lots high/low supplemented with copper (7A). Lactate profile of production shake flask cultures using TC yeastolate lots high/low supplemented with copper (7B). pH profile of production shake flask cultures using TC yeastolate lots high/low supplemented with copper (7C).

Figure 8:
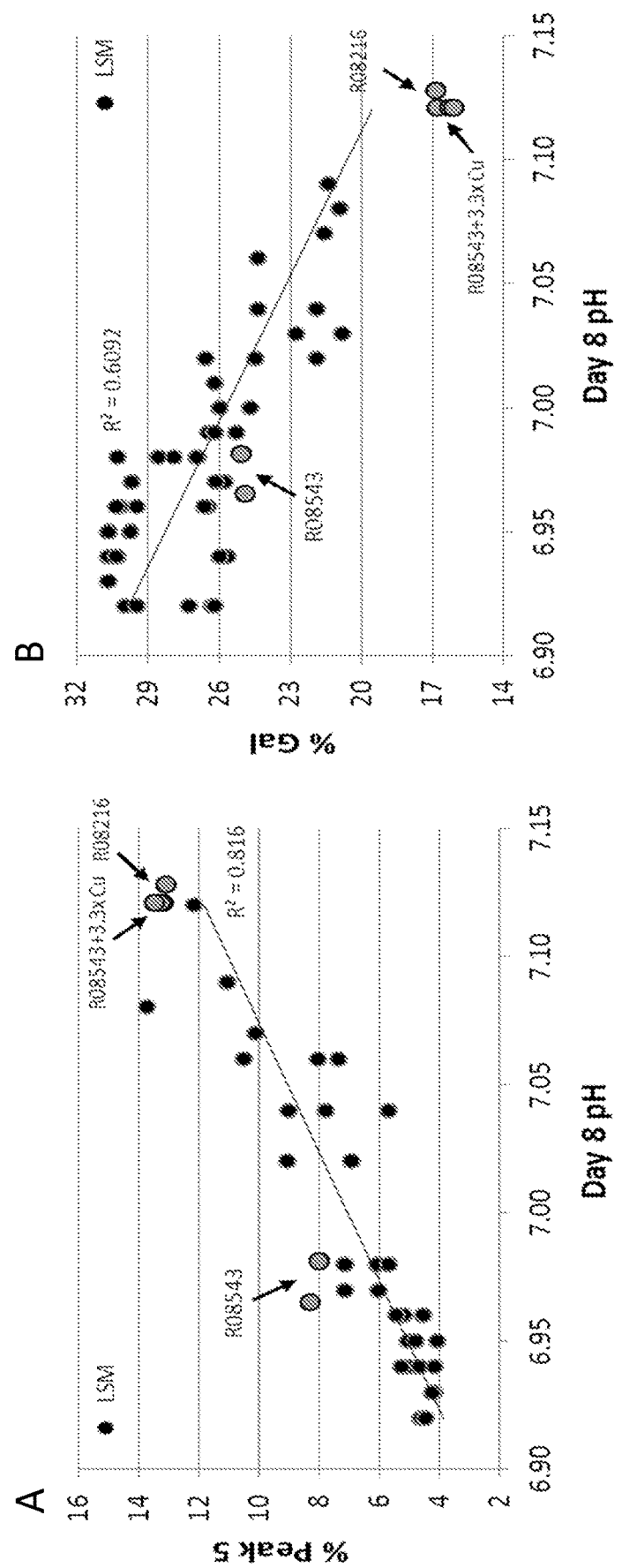

FIGS. 8A-8B. % Peak 5 was plotted against Day 8 pH of production shake flask cultures using TC yeastolate lots (8A). % Gal was plotted against Day 8 pH of production shake flask cultures using TC yeastolate lots (8B). Shake flask results plotted with large scale manufacturing (LSM) data.

Figure 9:
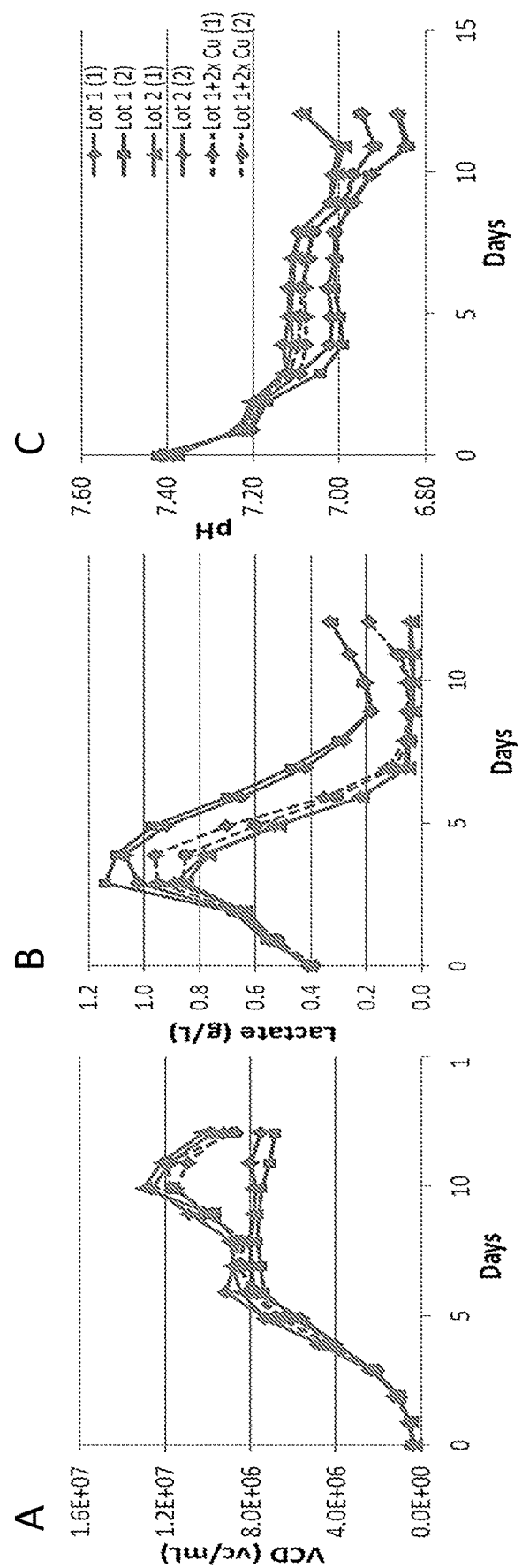

FIGS. 9A-9C. Impact of copper levels on the viable cell density (VCD) profile of production shake flask cultures using Bio Springer yeastolate lots high/low supplemented with copper (9A). Impact of copper levels on lactate levels of production shake flask cultures using Bio Springer yeastolate lots high/low supplemented with copper (9B). Impact of copper levels on pH of production shake flask cultures using Bio Springer yeastolate lots high/low supplemented with copper (9C).

Figure 10:
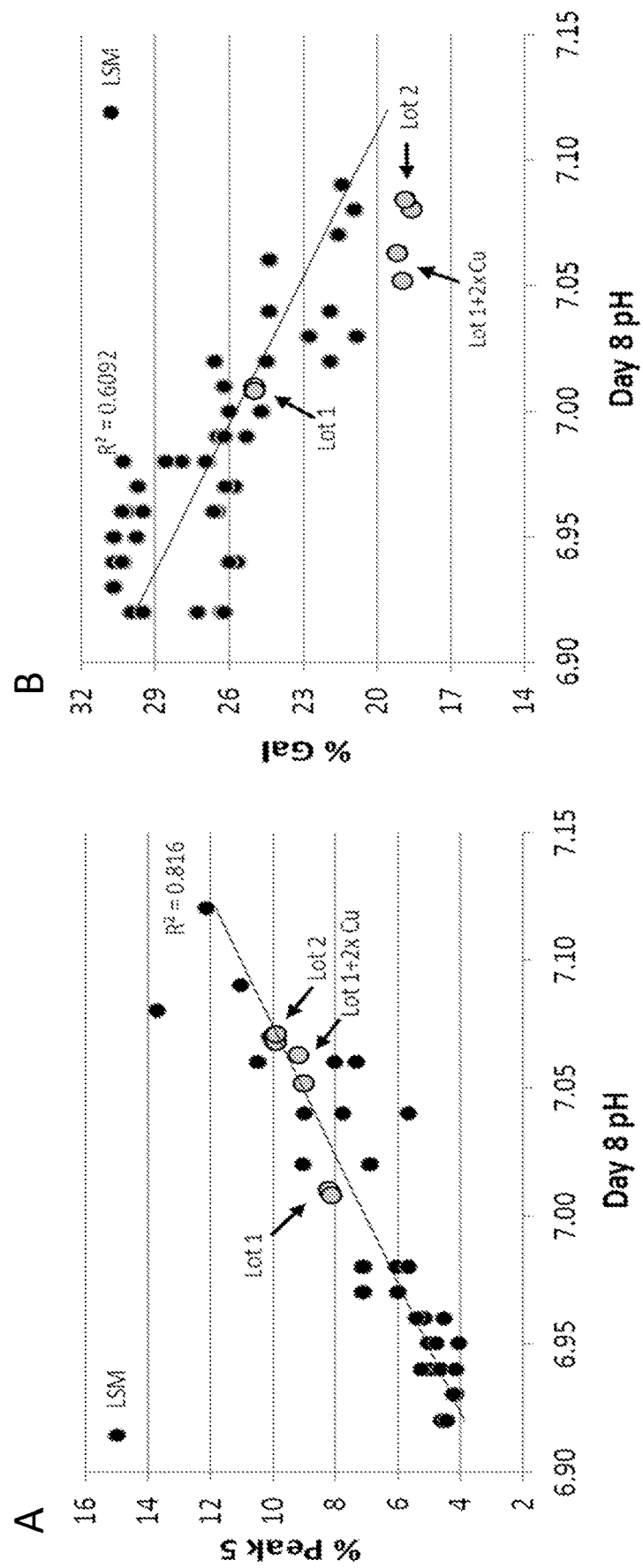

FIGS. 10A-10B. Impact of copper levels on Peak 5 levels on Day 8 of production shake flask cultures using Bio Springer yeastolate lots (10A). Impact of copper levels on Gal levels on Day 8 of production shake flask cultures using Bio Springer yeastolate lots (10B). Shake flask results plotted with large scale manufacturing (LSM) data.

Figure 11:
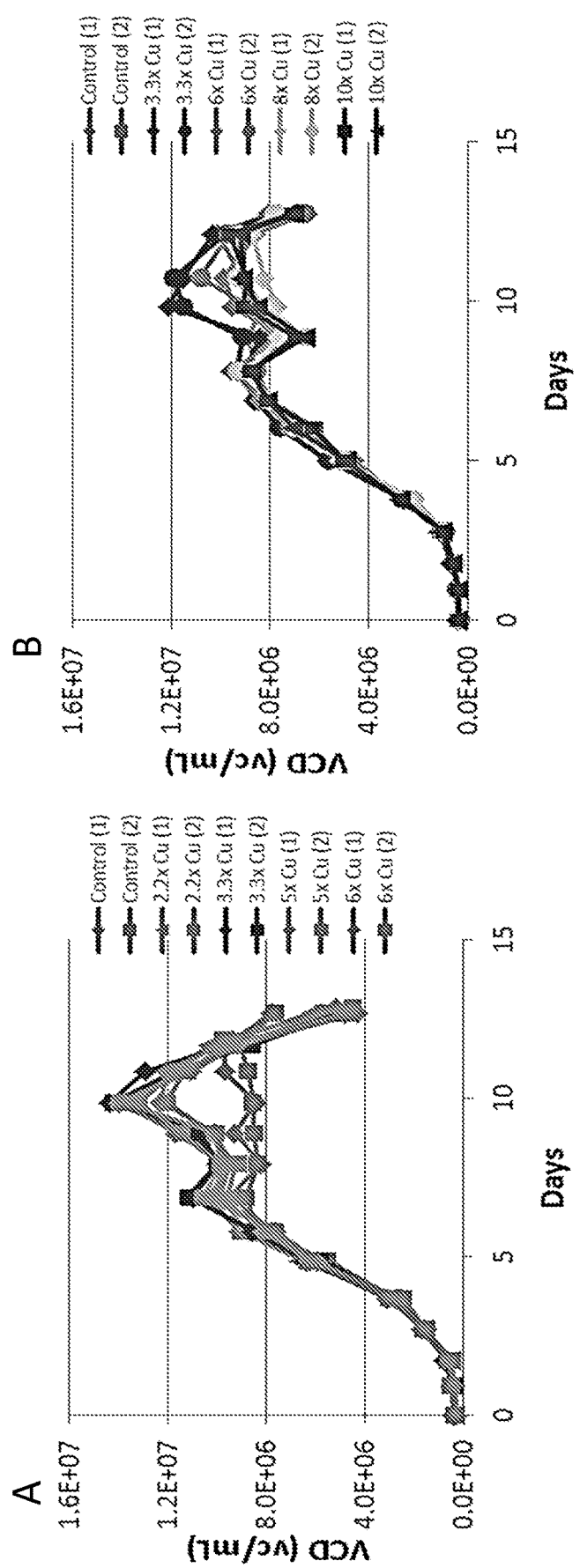

FIGS. 11A-11B. Impact of copper levels on cell growth in production shake flasks. The VCD results for Experiment 1 (11A). The VCD results for Experiment 2 (11B).

Figure 12:
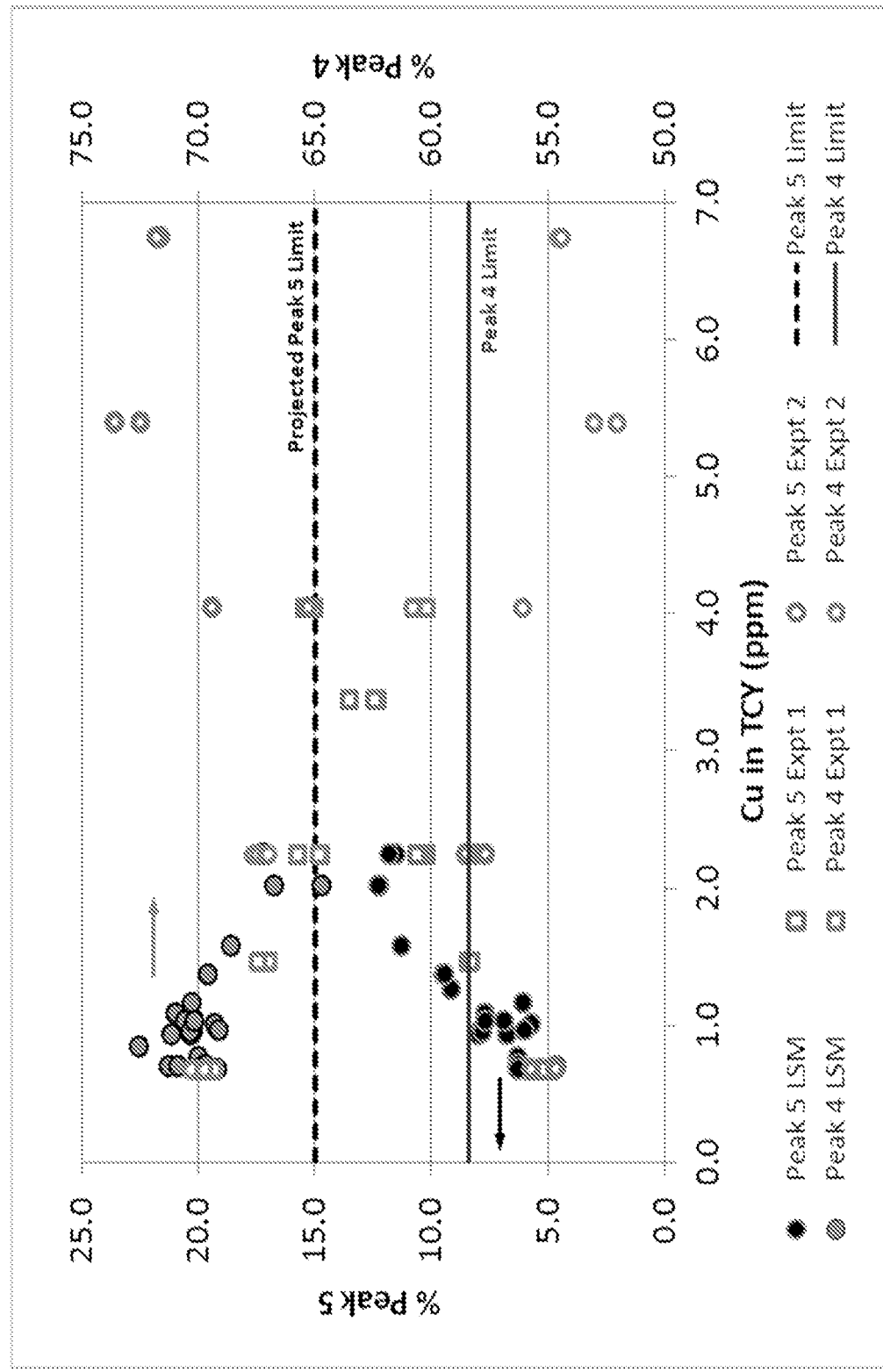

FIG. 12. Correlation between Peak5/Peak 4 and copper concentrations in TC yeastolate.

Figure 13:
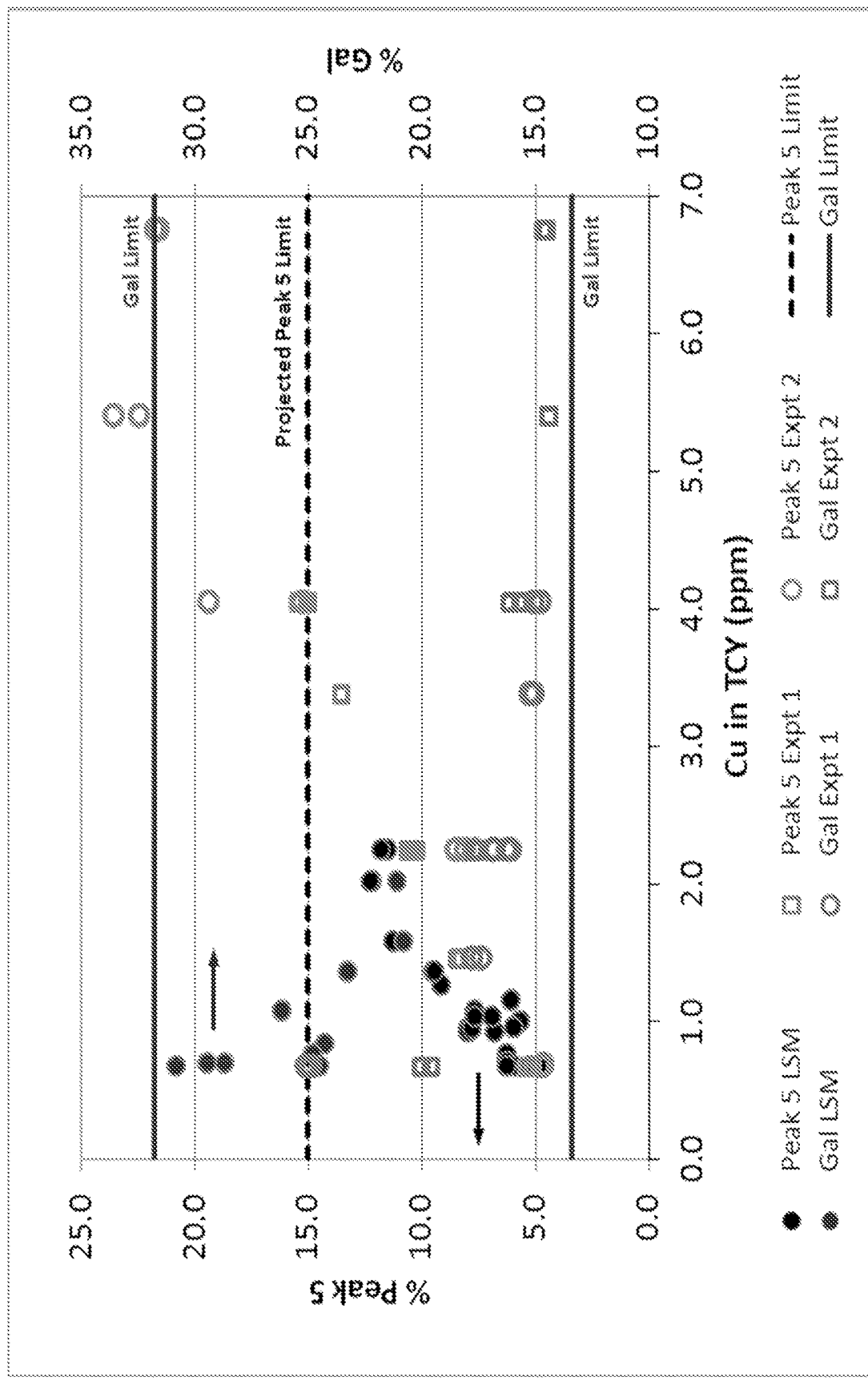

FIG. 13. Correlation between Peak5/Gal and copper concentrations in TC yeastolate.

Figure 14:
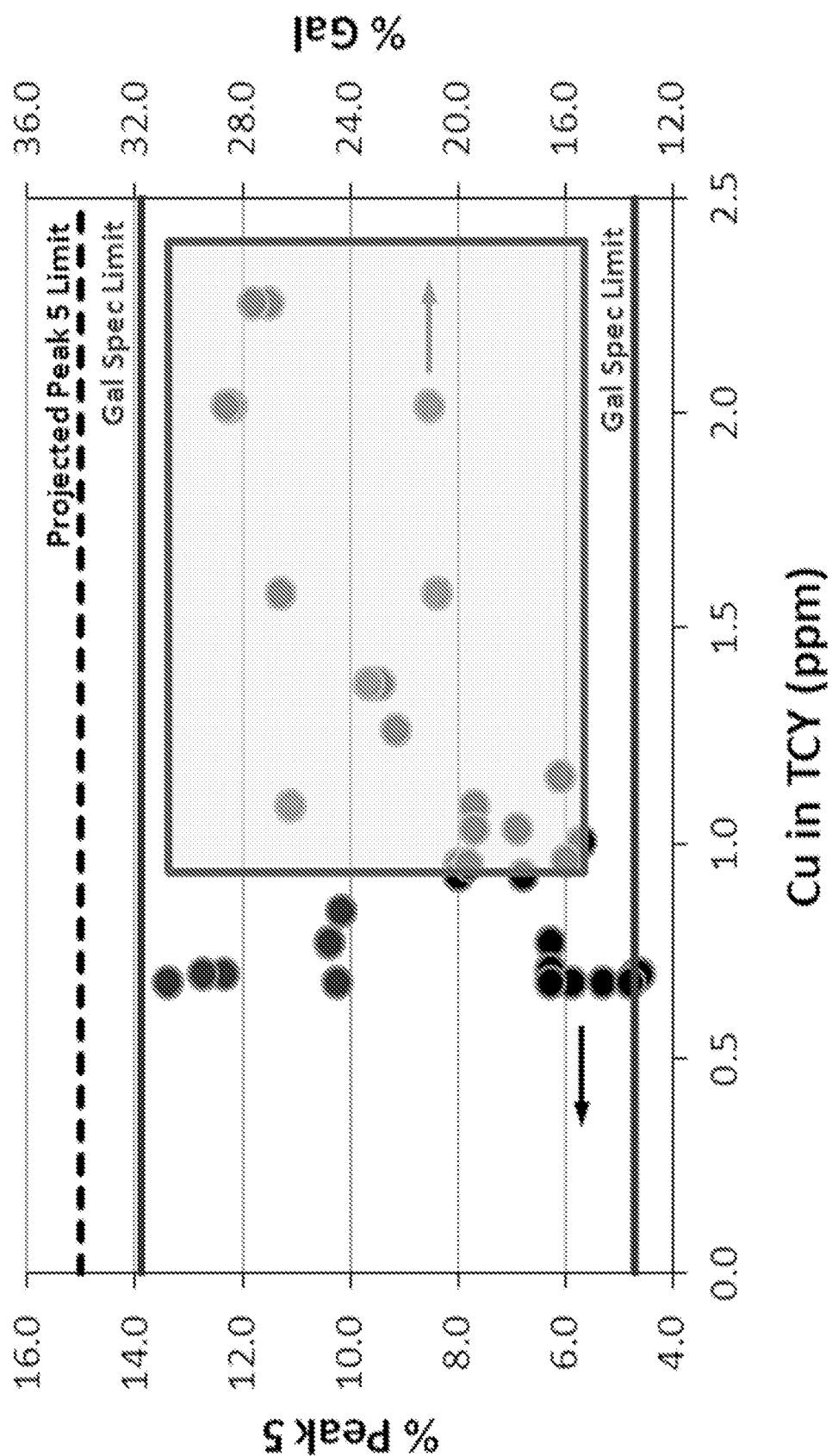

FIG. 14. Impact of copper in TC yeastolate on Peak 5 and Gal levels. The highlighted region specifies the target copper range.

Figure 15:
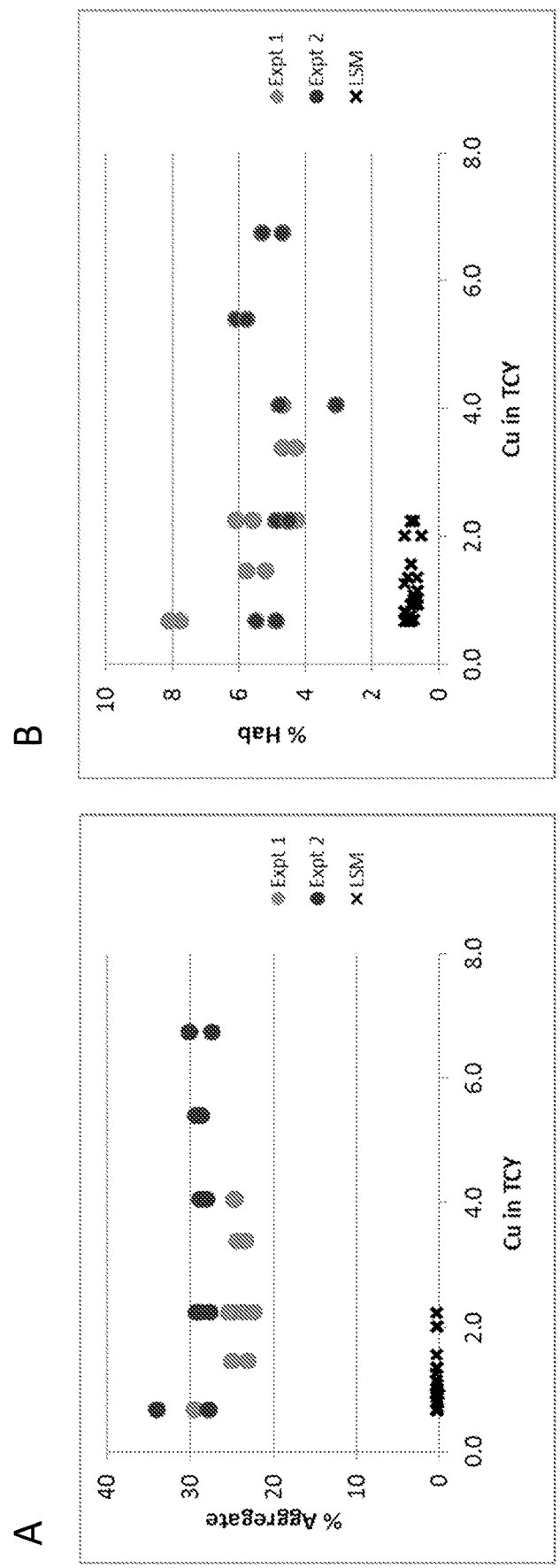
Figure 16:
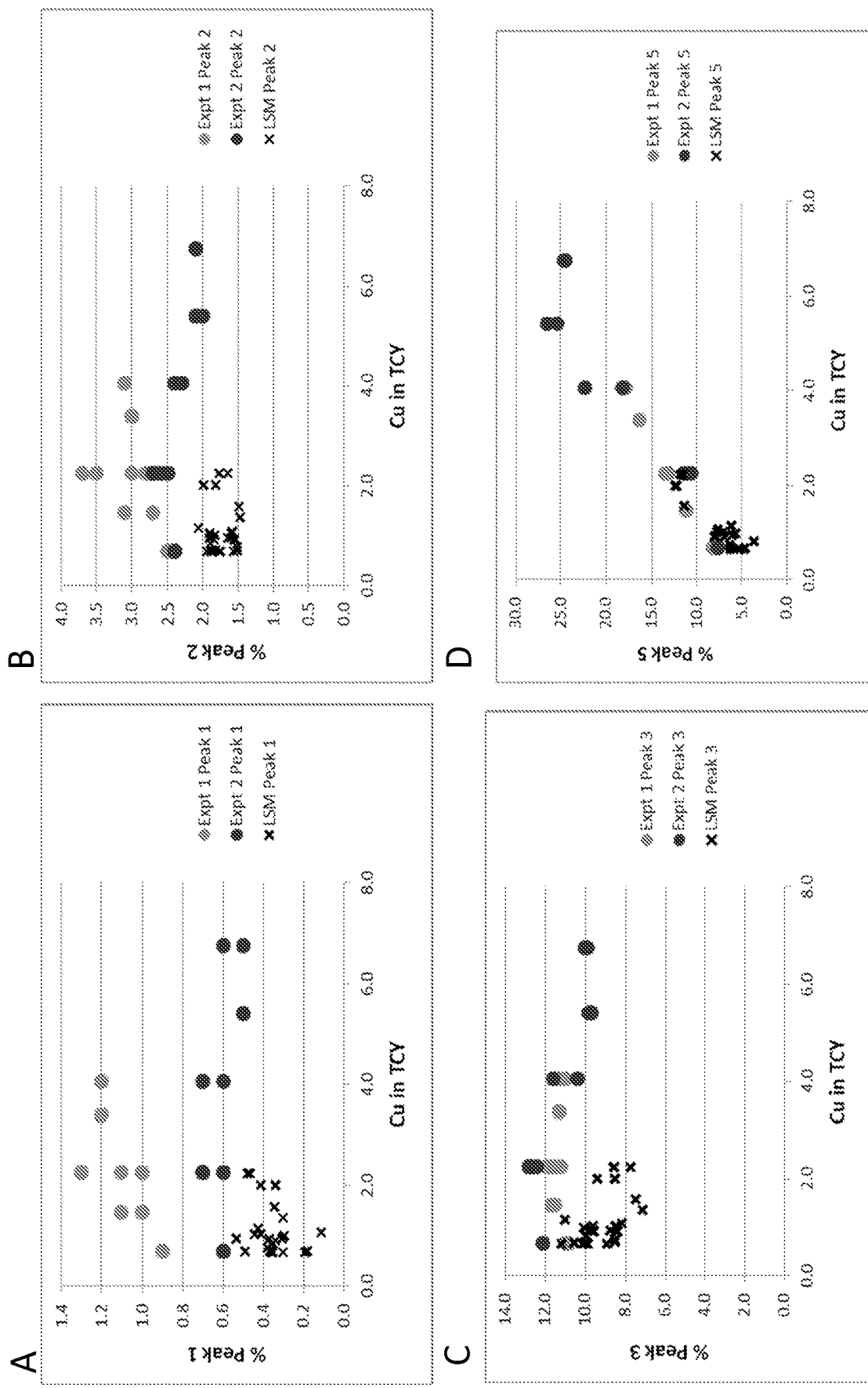
Figure 16:
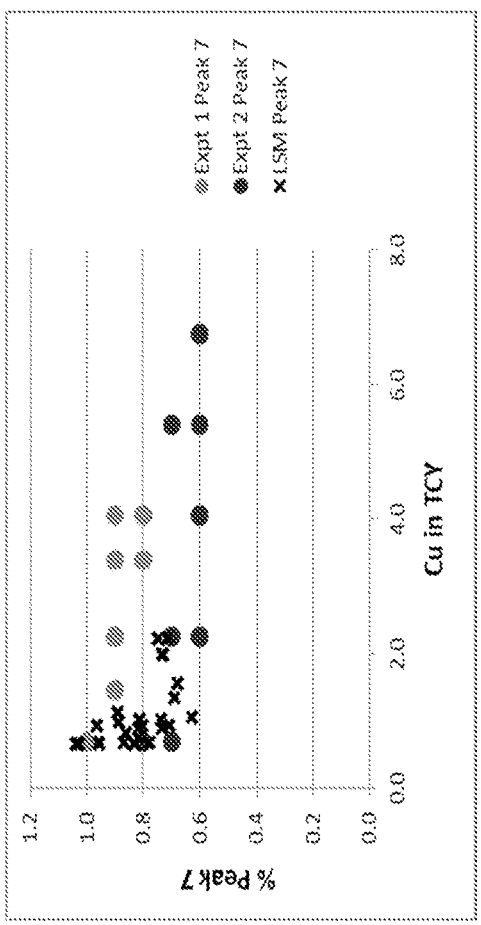
Figure 16:
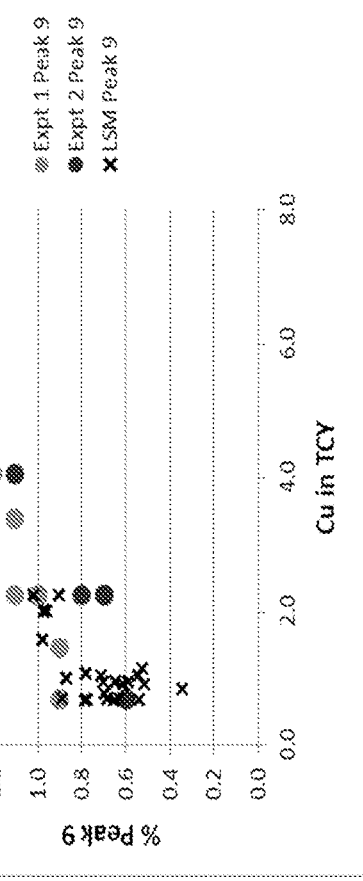
Figure 16:
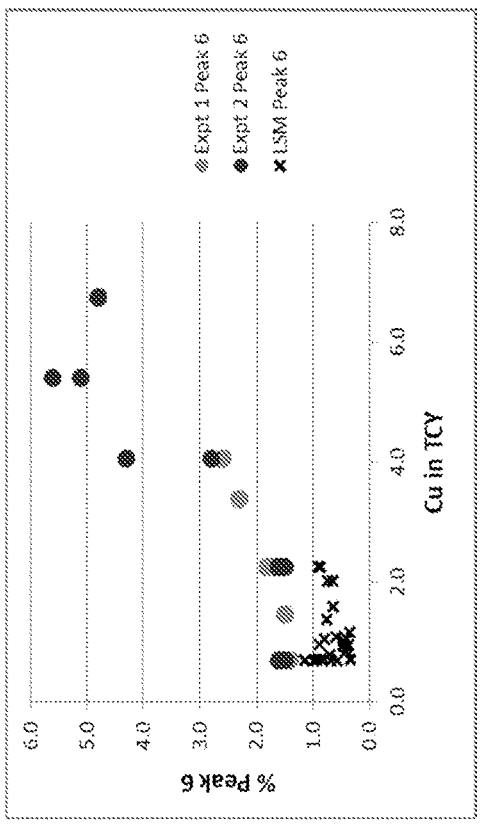
Figure 16:
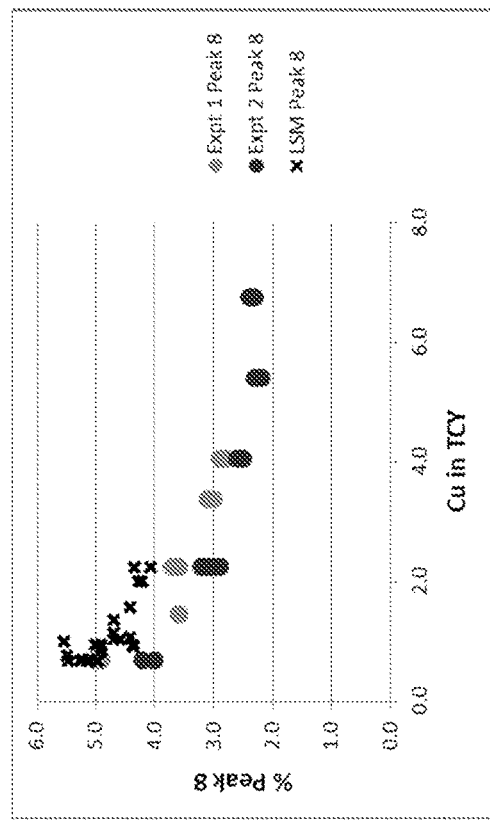
Figure 16:
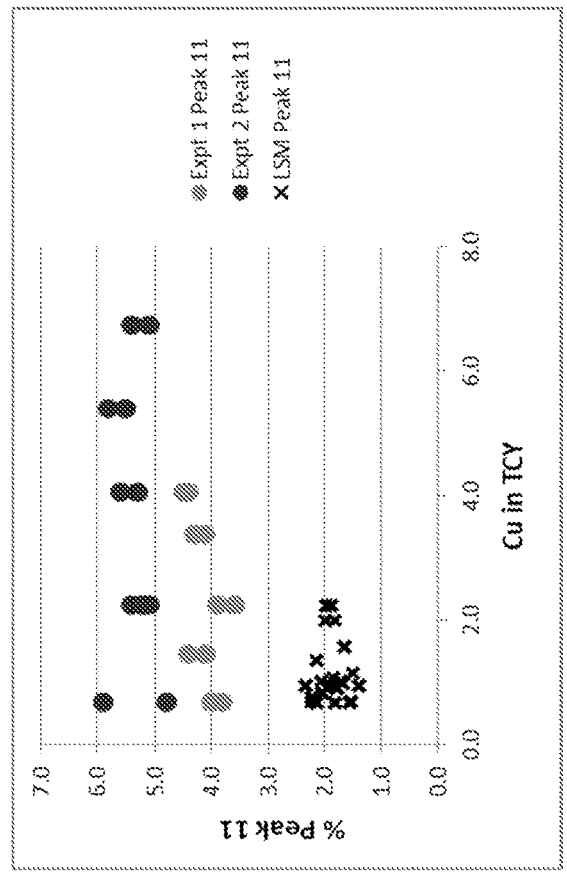
Figure 16:
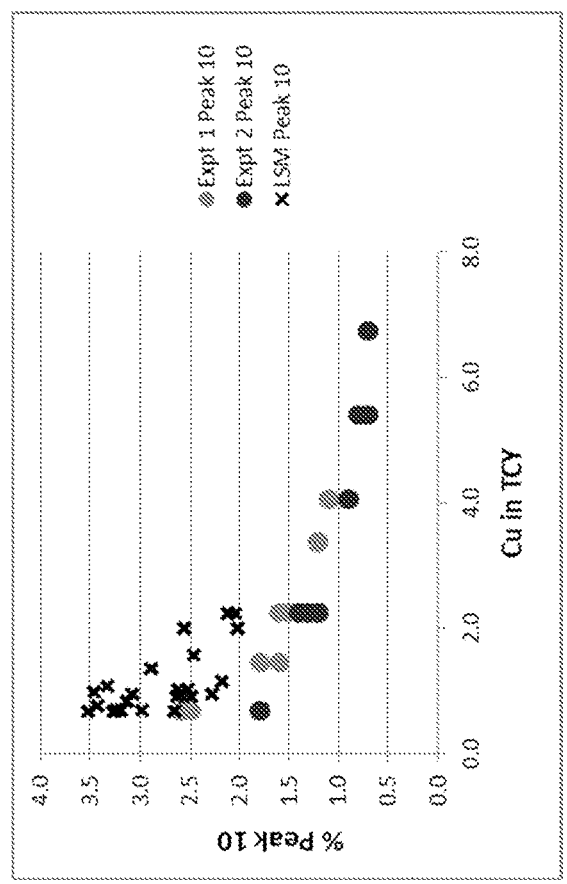

FIGS. 15A-15B. Impact of copper levels in yeastolate on % Aggregate (5A) and % Half Antibody (5B).

FIGS. 16A-16J. Impact of copper levels in yeastolate on IEC peaks 1-11 respectively.

DETAILED DESCRIPTION OF THE INVENTION

The present invention is based on the recognition that cell culture media supplemented with copper provides the ability to control and manipulate the glycolsylation patterns of recombinant glycoproteins produced in eukaryotic cell cultures. Such glyclosylation patterns include, without limitation, the level of galactosylation, and variations in isoform levels.

The present invention is also applicable to modifying the glycosylation of a recombinant glycoprotein of interest such that it falls within the quality attribute ranges for the desired product. For example, the present invention is applicable to modifying the glycosylation profile of a recombinant glycoprotein of interest to more closely resemble, match, or substantially match the glycosylation pattern of a reference sample of the same glycoprotein. Differences between various manufacturing processes can result in glycoproteins with identical amino acid sequences having different glycosylation patterns depending on, for example, conditions for growth, cell line used to express the glycoprotein, etc.

Provided herein are methods for achieving a predetermined glycosylation profile of a recombinant glycoprotein of interest comprising adjusting the concentration of copper in a cell culture to achieve a target concentration range, wherein the cell culture comprises host cells producing the recombinant glycoprotein of interest. Also provided herein are methods for optimizing a cell culture medium for the production of a recombinant glycoprotein of interest comprising (i) determining the amount of copper in a cell culture medium or a component used to produce a cell culture medium, and (ii) adjusting the concentration of copper in the cell culture medium to achieve an amount of copper within the target range, wherein the target range is sufficient to produce the recombinant glycoprotein of interest with a predetermined galactosylation profile. Finally, provided herein are methods for obtaining a component for a cell culture medium comprising (i) measuring the amount of copper in a hydrolysate from yeast and (ii) if the amount of copper is below a target range, supplementing the yeast hydrolysate with copper to achieve an amount of copper within the target range.

I. Definitions

As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described with the language "comprising," otherwise analogous embodiments described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various embodiments of the disclosure, which can be had by reference to the specification as a whole. Accordingly, the terms defined immediately below are more fully defined by reference to the specification in its entirety.

The terms "polypeptide" or "protein" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit.

The term "glycoprotein" refers to a polypeptide or protein coupled to at least one carbohydrate moiety, e.g., a polysaccharide or an oligosaccharide, that is attached to the protein via an oxygen-containing or a nitrogen-containing side chain of an amino acid residue, e.g., a serine or threonine residue ("O-linked") or an asparagine residue ("N-linked"). The term "glycan" refers to a polysaccharide or an oligosaccharide, e.g., a polymer comprised of monosaccharides. Glycans can be homo- or heteropolymers of monosaccharide residues, and can be linear or branched.

As used herein, the "glycosylation pattern" of a recombinant glycoprotein of interest refers to various physical characteristics of the glycoprotein's polysaccharides or oligosaccharides, such as, e.g., the quantity and quality of various monosaccharides present, the degree of branching, and/or the attachment (e.g., N-linked or O-linked). The "glycosylation pattern" of a glycoprotein can also refer to the functional characteristics imparted by the glycoprotein's oligosaccharides and polysaccharides. For example, the extent to which the glycoprotein can bind to FcγRIIIa and induce antibody-dependent cellular cytotoxicity (ADCC).

"Fucosylation" refers to the degree and distribution of fucose residues on polysaccharides and oligosaccharides, for example, N-glycans, O-glycans and glycolipids. Therapeutic glycoproteins, e.g., antibodies or Fc fusion proteins, with non-fucosylated, or "afucosylated" N-glycans exhibit dramatically enhanced antibody-dependent cellular cytotoxicity (ADCC) due to the enhancement of FcγRIIIa binding capacity without any detectable change in complement-dependent cytotoxicity (CDC) or antigen binding capability. In certain situations, e.g., cancer treatment, non-fucosylated or "afucosylated" antibodies are desirable because they can achieve therapeutic efficacy at low doses, while inducing high cellular cytotoxicity against tumor cells, and triggering high effector function in NK cells via enhanced interaction with FcγRIIIa. In other situations, e.g., treatment of inflammatory or autoimmune diseases, enhanced ADCC and FcγRIIIa binding is not desirable, and accordingly therapeutic glycoproteins with higher levels of fucose residues in their N-glycans can be preferable. As used herein, the term "% afucose" refers to the percentage of non-fucosylated N-glycans present on a recombinant glycoprotein of interest. A higher % afucose denotes a higher number of non-fucosylated N-glycans, and a lower % afucose denotes a higher number of fucosylated N-glycans.

"Sialylation" refers to the type and distribution of sialic acid residues on polysaccharides and oligosaccharides, for example, N-glycans, O-glycans and glycolipids. Sialic acids are most often found at the terminal position of glycans. Sialylation can significantly influence the safety and efficacy profiles of these proteins. In particular, the in vivo half-life of some biopharmaceuticals correlates with the degree of oligosaccharide sialylation. Furthermore, the sialylation pattern can be a very useful measure of product consistency during manufacturing.

The two main types of sialyl residues found in biopharmaceuticals produced in mammalian expression systems are N-acetyl-neuraminic acid (NANA) and N-glycolyl-neuraminic acid (NGNA). These usually occur as terminal structures attached to galactose (Gal) residues at the non-reducing terminii of both N- and O-linked glycans.

"Galactosylation" refers to the type and distribution of galactose residues on polysaccharides and oligosaccharides. Galactose refers to a group of monosaccharides which include open chain and cyclic forms. An important disaccharide form of galactose is galactose-alpha-1,3-galactose ($\alpha$-gal).

The term "undesirable side effects" refers to certain aspects and results of glycosylation which, under certain circumstances, are to be minimized or avoided. In certain aspects, a side effect to be reduced or avoided is a substantial increase in the level of $\alpha$-gal. In another aspect a side effect to be reduced or avoided is a substantial reduction in sialic acid levels. In various aspects the methods described herein achieve certain glycosylation patterns without substantially affecting culture density, cell viability level, or both. In certain aspects, a "side effect" which might be undesirable in one glycoprotein, e.g., a decrease in fucose levels (increases ADCC and Fc$\gamma$RIIIa binding) in an antibody used to treat an inflammatory disease, might be desirable in another glycoprotein, e.g., in an antibody used to treat cancer.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

"Recombinantly expressed glycoprotein" and "recombinant glycoprotein" as used herein refer to a glycoprotein expressed from a host cell that has been genetically engineered to express that glycoprotein. The recombinantly expressed glycoprotein can be identical or similar to glycoproteins that are normally expressed in the mammalian host cell. The recombinantly expressed glycoprotein can also be foreign to the host cell, i.e. heterologous to peptides normally expressed in the mammalian host cell. Alternatively, the recombinantly expressed glycoprotein can be chimeric in that portions of the glycoprotein contain amino acid sequences that are identical or similar to glycoproteins normally expressed in the mammalian host cell, while other portions are foreign to the host cell. In certain embodiments, the recombinant glycoprotein comprises an antibody or fragments thereof. As used herein, the terms "recombinantly expressed glycoprotein" and "recombinant glycoprotein" also encompasses an antibody produced by a hybridoma.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization, Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein, Sambrook et al., Molecular Cloning: A Laboratory Manual, pp. 18.1-18.88 (Cold Spring Harbor Laboratory Press, 1989).

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The primary cells for mediating ADCC, NK cells, express Fc$\gamma$RIII only, whereas monocytes express Fc$\gamma$RI, Fc$\gamma$RII and Fc$\gamma$RIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of a molecule of interest may be assessed in vivo, e.g., in an animal model such as that disclosed in Clynes et al. PNAS (USA) 95:652-656 (1998).

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased Clq binding capability are described, e.g., in U.S. Pat. No. 6,194,551 B1 and WO 1999/51642. See also, e.g., Idusogie et al. J. Immunol. 164: 4178-4184 (2000).

The term "basal media formulation" or "basal media" as used herein refers to any cell culture media used to culture cells that has not been modified either by supplementation, or by selective removal of a certain component.

As used herein, the terms "additive" or "supplement" refer to any supplementation made to a basal medium to achieve the goals described in this disclosure. An "additive"

or "supplement" can include a single substance, e.g., copper II sulfate, or can include multiple substances, e.g., various copper salts. The terms "additive" or "supplement" refer to the all of the components added, even though they need not be added at the same time, and they need not be added in the same way. For example, one or more components of an "additive" or "supplement" can be added as a single bolus or two or more boli from a stock solution, while other components of the same "additive" or "supplement" can be added as part of a feed medium. In addition, any one or more components of an "additive" or "supplement" can be present in the basal medium from the beginning of the cell culture.

The terms "culture", "cell culture" and "eukaryotic cell culture" as used herein refer to a eukaryotic cell population, either surface-attached or in suspension that is maintained or grown in a medium (see definition of "medium" below) under conditions suitable to survival and/or growth of the cell population. As will be clear to those of ordinary skill in the art, these terms as used herein can refer to the combination comprising the mammalian cell population and the medium in which the population is suspended.

The terms "media", "medium", "cell culture medium", "culture medium", "tissue culture medium", "tissue culture media", and "growth medium" as used herein refer to a solution containing nutrients, which nourish growing cultured eukaryotic cells. Typically, these solutions provide essential and non-essential amino acids, vitamins, energy sources, lipids, and trace elements required by the cell for minimal growth and/or survival. The solution can also contain components that enhance growth and/or survival above the minimal rate, including hormones and growth factors. The solution is formulated to a pH and salt concentration optimal for cell survival and proliferation. The medium can also be a "defined medium" or "chemically defined medium"—a serum-free medium that contains no proteins, hydrolysates or components of unknown composition. Defined media are free of animal-derived components and all components have a known chemical structure. One of skill in the art understands a defined medium can comprise recombinant glycoproteins or proteins, for example, but not limited to, hormones, cytokines, interleukins and other signaling molecules.

The cell culture medium is generally "serum free" when the medium is essentially free of serum, or fractions thereof, from any mammalian source (e.g. fetal bovine serum (FBS)). By "essentially free" is meant that the cell culture medium comprises between about 0-5% serum, preferably between about 0-1% serum, and most preferably between about 0-0.1% serum. Advantageously, serum-free "defined" medium can be used, wherein the identity and concentration of each of the components in the medium is known (i.e., an undefined component such as bovine pituitary extract (BPE) is not present in the culture medium).

The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

The term "cell density" as used herein refers to that number of cells present in a given volume of medium.

The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

The term "fed-batch culture" as used herein refers to a method of culturing cells in which additional components are provided to the culture at some time subsequent to the beginning of the culture process. A fed-batch culture can be started using a basal medium. The culture medium with which additional components are provided to the culture at some time subsequent to the beginning of the culture process is a feed medium. A fed-batch culture is typically stopped at some point and the cells and/or components in the medium are harvested and optionally purified.

The term "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 liter and can be 10, 50, 100, 250, 500, 1000, 2000, 2500, 3000, 5000, 8000, 10,000, 12,0000, 15,000, 20,000, 30,000 liters or more, or any volume in between. For example, a bioreactor will be 10 to 5,000 liters, 10 to 10,000 liters, 10 to 15,000 liters, 10 to 20,000 liters, 10 to 30,000 liters, 50 to 5,000 liters, 50 to 10,000 liters, 50 to 15,000 liters, 50 to 20,000 liters, 50 to 30,000 liters, 1,000 to 5,000 liters, or 1,000 to 3,000 liters. A bioreactor can be a stirred-tank bioreactor or a shake flask. The internal conditions of the bioreactor, for example, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the glycoprotein or protein of interest. The volume of the large-scale cell culture production bioreactor is typically at least 500 liters and can be 1000, 2000, 2500, 5000, 8000, 10,000, 12,0000, 15,000 liters or more, or any volume in between. For example, the large scale cell culture reactor will be between about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a large scale cell culture reactor will be at least about 500 liters, at least about 1,000 liters, at least about 2,000 liters, at least about 3,000 liters, at least about 5,000 liters, at least about 10,000 liters, at least about 15,000 liters, or at least about 20,000 liters. One of ordinary skill in the art will be aware of and will be able to choose suitable bioreactors for use in practicing the present invention.

The term "stirred-tank bioreactor" as used herein refers to any vessel used for the growth of a mammalian cell culture that has an impeller.

The term "shake flask" as used herein refers to any vessel used for the growth of a mammalian cell culture that does not have an impeller.

The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature*, 537:3053 (1983)).

The term "osmolality" is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of water (1 mOsm/kg $H_2O$ at 38° C. is equivalent to an osmotic pressure of 19 mm Hg). "Osmolarity" refers to the number of solute particles dissolved in 1 liter of solution. Solutes which can be added to the culture medium so as to increase the osmolality thereof include proteins, peptides, amino acids, non-metabolized polymers, vitamins, ions, salts, sugars, metabolites, organic acids, lipids, etc. In the preferred embodiment, the concentration of amino acids and NaCl in the culture medium is increased in order to achieve the desired osmolality ranges set forth herein. When used herein, the abbreviation "mOsm" means "milliosmoles/kg $H_2O$".

The term "titer" as used herein refers to the total amount of recombinantly expressed glycoprotein or protein produced by a cell culture divided by a given amount of medium volume. Titer is typically expressed in units of milligrams of glycoprotein or protein per milliliter of medium or in units of grams of glycoprotein or protein per liter of medium.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., cellular viability). The difference between said two values is, for example, less than about 50%, less than about 40%, less than about 30%, less than about 20%, and/or less than about 10% as a function of the reference/comparator value.

The phrase "substantially reduced," or "substantially different," as used herein with regard to amounts or numerical values (and not as reference to the chemical process of reduction), denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., cellular viability). The difference between said two values is, for example, greater than about 10%, greater than about 20%, greater than about 30%, greater than about 40%, and/or greater than about 50% as a function of the value for the reference/comparator molecule.

II. Supplementation of Cell Culture Medium to Control Glycosylation Patterns

Provided herein are methods to culture eukaryotic cells engineered to express a recombinant glycoprotein of interest. Specifically this disclosure provides methods for controlling the glycosylation patterns of a recombinant glycoprotein of interest by supplementing a tissue culture medium in which the cells are growing and/or producing the recombinant glycoprotein of interest with an additive, or culturing eukaryotic cells engineered to express a glycoprotein of interest in a tissue culture medium, which has been supplemented with such an additive. In certain embodiments, glycoproteins produced by the methods provided are recovered. The methods are based on the recognition that growth of cells expressing a recombinant glycoprotein of interest in cell culture medium supplemented with copper can result in alterations to eukaryotic cell glycosylation patterns, such as the level of galactosylation. In certain embodiments, the copper added is copper (II) sulfate. In certain embodiments, the alteration of the glycosylation pattern of the recombinant glycoprotein of interest comprises a reduced level of galactosylation. In one embodiment, the recombinant glycoprotein of interest comprises a predetermined galactosylation profile. In another embodiment, the recombinant glycoprotein of interest comprising a predetermined galactosylation profile is an anti-α4-integrin antibody. In another embodiment, the predetermined galactosylation profile of the anti-α4-integrin antibody comprises 10 to 35% galactosylation, 10 to 30% galactosylation, 10 to 20% galactosylation, 10 to 15% galactosylation, 15 to 35% galactosylation, 20 to 35% galactosylation, 25 to 35% galactosylation, or 30 to 35% galactosylation. In another embodiment, the predetermined galactosylation profile of the anti-α4-integrin antibody comprises 13 to 32% galactosylation. In another embodiment, the predetermined galactosylation profile of the anti-α4-integrin antibody comprises 13.4 to 31.8% galactosylation. In another embodiment, the predetermined galactosylation profile of the anti-α4-integrin antibody comprises 15 to 31% galactosylation. In another embodiment, the predetermined galactosylation profile of the anti-α4-integrin antibody comprises 20 to 28% or 22 to 25% galactosylation. In another embodiment, the predetermined galactosylation profile of the anti-α4-integrin antibody comprises about 10, 11, 12, 13, 14, 15, 16, 17, 18, 19, 20, 21, 22, 23, 24, 25, 26, 27, 28, 29, 30, 31, 32, 33, 34, or 35% galactosylation. In another embodiment, the predetermined galactosylation profile of the anti-α4-integrin antibody comprises 25% galactosylation.

In one embodiment, the copper concentration in the cell culture alters the levels of the isoform variants of the anti-α4-integrin antibody. In one embodiment, the copper concentration in the cell culture alters the level of the Peak 4 isoform of the anti-α4-integrin antibody. In one embodiment, the copper concentration in the cell culture alters the level of the Peak 5 isoform of the anti-α4-integrin antibody. In one embodiment, the copper concentration in the cell culture alters the level of the Peak 6 isoform of the anti-α4-integrin antibody. In one embodiment, the copper concentration in the cell culture In one embodiment, the copper concentration in the cell culture alters the level of the Peak 8 isoform of the anti-α4-integrin antibody. In one embodiment, the copper concentration in the cell culture alters the level of the Peak 9 isoform of the anti-α4-integrin antibody. In one embodiment, the copper concentration in the cell culture alters the level of the Peak 10 isoform of the anti-α4-integrin antibody.

The present invention is applicable to altering, manipulating, or controlling the glycosylation pattern of a recombinant glycoprotein of interest to match, substantially match, approach, or more closely resemble the glycosylation pattern of the same glycoprotein, but produced in a different cell culture system. Recombinant glycoproteins of interest can be produced according to the invention using various different cell culture systems, e.g., a batch culture, fed-batch culture a perfusion culture, a shake flask, and/or a bioreactor. In one embodiment, cells expressing a recombinant glycoprotein of interest are cultured in basal medium to which the additive is introduced as a bolus, or two or more boli, from a stock solution. In another embodiment, the additive is introduced as a component of a feed medium. In certain embodiments the cell culture comprises a growth phase and a protein production phase, and the additive is introduced into the culture medium before, or at the same time as, or at some point after the initiation of the protein production phase.

In one embodiment, a medium described herein is a serum-free medium, animal protein-free medium or a chemically-defined medium. In a specific embodiment, a medium described herein is a chemically-defined medium.

In certain embodiments, the method comprises adding $CuSO_4$. $CuSO_4$ can be added to the culture medium in one bolus or two or more boli from a stock solution to, or be added as a component of a feed medium achieve a $CuSO_4$ concentration in the culture medium of between about 0.01 mM and about 1 mM $CuSO_4$. In certain embodiments the additive comprises $CuSO_4$, which can be added to the culture medium in one bolus or two or more boli from a stock solution, or be added as a component of a feed medium to achieve a $CuSO_4$ concentration in the culture medium between about 0.01 mM and about 1 mM, about 0.01 mM and about 0.5 mM, about 0.01 mM and about 0.25 mM, about 0.01 mM and about 0.2 mM, about 0.01 mM and about 0.1 mM, about 0.01 mM and about 0.05 mM, about 0.02 mM and about 1 mM, about 0.05 mM and about 1 mM, about 0.1 mM and about 1 mM, about 0.2 mM and about 1 mM, about 0.5 mM and about 1 mM, about 0.2 mM and about 0.5 mM, or about 0.02 mM and about 0.05 mM. In another embodiment, the target copper concentration in the culture medium is between 0.02 mM and 0.05 mM at Day 0. In another embodiment, the target copper concentration in the culture mediums is between 0.2 mM and 0.5 mM at Day 11. In another embodiment, the copper concentration is constantly monitored and maintained within the target copper concentration range. In another embodiment, the target concentration is maintained through a feedback loop.

In another embodiment, the concentration of copper added to the cell culture is about 1.0 ppm to 2.5 ppm, about 1.1 ppm to 2.5 ppm, about 1.2 ppm to 2.5 ppm, about 1.3 ppm to 2.5 ppm, about 1.4 ppm to 25 ppm, about 1.5 ppm to 2.5 ppm, about 1.6 ppm to 2.5 ppm, about 1.7 ppm to 2.5 ppm, about 1.8 ppm to 2.5 ppm, about 1.9 ppm to 2.5 ppm, about 2.0 ppm to 2.5 ppm, about 2.2 ppm to 2.5 ppm, about 2.3 ppm to 2.5 ppm, about 2.4 ppm to 2.5 ppm, about 1.0 ppm to 2.4 ppm, about 1.0 ppm to 2.3 ppm, about 1.0 ppm to 2.2 ppm, about 1.0 ppm to 2.1 ppm, about 1.0 ppm to 2.0 ppm, about 1.0 ppm to 1.9 ppm, about 1.0 ppm to 1.8 ppm, about 1.0 ppm to 1.7 ppm, about 1.0 ppm to 1.6 ppm, about 1.0 ppm to 1.5 ppm, about 1.0 ppm to 1.4 ppm, about 1.0 ppm to 1.3 ppm, about 1.0 ppm to 1.2 ppm, or about 1.0 ppm to 1.1 ppm. In another embodiment, the concentration of copper added to the cell culture is 1.0 ppm to 2.4 ppm.

III. Cell Culture Compositions

The present invention further provides a cell culture composition comprising a medium described herein and cells, produced by the methods provided herein.

In one embodiment, a cell culture composition produced by the provided methods can be a batch culture, fed-batch culture or a perfusion culture. In a specific embodiment, a cell culture composition of the invention is a fed batch culture.

In one embodiment, a cell culture composition produced by the provided methods comprises eukaryotic cells. In another embodiment, a cell culture composition produced by the provided methods comprises mammalian cells selected from the group consisting of CHO cells, HEK cells, NSO cells, PER.C6 cells, 293 cells, HeLa cells, and MDCK cells. In a specific embodiment, a cell culture composition described herein comprises CHO cells. In another specific embodiment, a cell culture composition described herein comprises HEK cells. In another specific embodiment, a cell culture composition described herein comprises hybridoma cells.

A cell culture composition produced by the provided methods can comprise cells that have been adapted to grow in serum free medium, animal protein free medium or chemically defined medium. Or it can comprise cells that have been genetically modified to increase their life-span in culture. In one embodiment, the cells have been modified to express an anti-α4-integrin antibody. In a further embodiment, the cells have been modified to express natalizumab.

The present invention provides a method of culturing cells, comprising contacting the cells with a medium disclosed herein, supplementing the medium as described above, or culturing cells in a medium supplemented as described above.

Cell cultures can be cultured in a batch culture, fed batch culture or a perfusion culture. In one embodiment, a cell culture according to a method of the present invention is a batch culture. In another embodiment, a cell culture according to a method of the present invention is a fed batch culture. In a further embodiment, a cell culture according to a method of the present invention is a perfusion culture. In certain embodiments the cell culture is maintained in a shake flask, in certain embodiments the cell culture is maintained in a bioreactor.

In one embodiment, a cell culture according to a method of the present invention is a serum-free culture. In another embodiment, a cell culture according to a method of the present invention is a chemically defined culture. In a further embodiment, a cell culture according to a method of the present invention is an animal protein free culture.

In one embodiment, a cell culture produced by the provided methods is contacted with a medium described herein during the growth phase of the culture. In another embodiment, a cell culture is contacted with a medium described herein during the production phase of the culture.

In one embodiment, a cell culture produced by the provided methods is contacted with a feed medium described herein during the production phase of the culture. In one embodiment, the culture is supplemented with the feed medium between about 1 and about 25 times during the second time period. In another embodiment, a culture is supplemented with the feed medium between about 1 and about 20 times, between about 1 and about 15 times, or between about 1 and about 10 times during the first time period. In a further embodiment, a culture is supplemented with the feed medium at least once, at least twice, at least three times, at least four times, at least five times, at least 6 times, at least 7 times, at least 8 times, at least 9 times, at least 10 times, at least 11 times, at least 12 times, at least 13 times, at least 14 times, at least 15 times, at least 20 times, at least 25 times. In a specific embodiment, the culture is a fed batch culture. In another specific embodiment, the culture is a perfusion culture.

A culture produced by the provided methods can be contacted with a feed medium described herein at regular intervals. In one embodiment, the regular interval is about once a day, about once every two days, about once every three days, about once every 4 days, or about once every 5 days. In a specific embodiment, the culture is a fed batch culture. In another specific embodiment, the culture is a perfusion culture.

A culture produced by the provided methods can be contacted with a feed medium described herein on an as needed basis based on the metabolic status of the culture. In one embodiment, a metabolic marker of a fed batch culture is measured prior to supplementing the culture with a feed medium described herein. In one embodiment, the metabolic marker is selected from the group consisting of: glucose concentration, lactate concentration, ammonium concentration, alanine concentration, glutamine concentration, glutamate concentration, cell specific lactate production rate to the cell specific glucose uptake rate ratio (LPR/GUR ratio), and Rhodamine 123 specific cell fluorescence. In one embodiment, an LPR/GUR value of >0.1 indicates the need to supplement the culture with a feed medium described herein. In a further specific embodiment, a lactate concentration of >3 g/L indicates the need to supplement the culture with a feed medium described herein. In another embodiment, a culture according to the present invention is supplemented with a feed medium described herein when the LPR/GUR value of the culture is >0.1 or when the lactate concentration of the culture is >3 g/L. In a specific embodiment, the culture is a fed batch culture. In another specific embodiment, the culture is a perfusion culture.

In one embodiment, a medium described herein is a feed medium for a fed batch cell culture. A skilled artisan understands that a fed batch cell culture can be contacted with a feed medium more than once. In one embodiment, a fed batch cell culture is contacted with a medium described herein only once. In another embodiment, a fed batch cell culture is contacted with a medium described herein more than once, for example, at least twice, at least three times, at least four times, at least five times, at least six times, at least seven times, or at least ten times.

In accordance with the present invention, the total volume of feed medium added to a cell culture should optimally be kept to a minimal amount. For example, the total volume of the feed medium added to the cell culture can be 1, 2, 3, 4, 5, 6, 7, 8, 9, 10, 15, 20, 25, 30, 35, 40, 45 or 50% of the volume of the cell culture prior to adding the feed medium.

Cell cultures produced by the provided methods can be grown to achieve a particular cell density, depending on the needs of the practitioner and the requirement of the cells themselves, prior to being contacted with a medium described herein. In one embodiment, the cell culture is contacted with a medium described herein at a viable cell density of 1, 5, 10, 15, 20, 25, 30, 35, 40, 45, 50, 55, 60, 65, 70, 75, 80, 85, 90, 95 or 99 percent of maximal viable cell density. In a specific embodiment, the medium is a feed medium.

Cell cultures produced by the provided methods can be allowed to grow for a defined period of time before they are contacted with a medium described herein. In one embodiment, the cell culture is contacted with a medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the cell culture. In another embodiment, the cell culture is contacted with a medium described herein at week 1, 2, 3, 4, 5, 6, 7, or 8 of the cell culture. In a specific embodiment, the medium is a feed medium.

Cell cultures produced by the provided methods can be cultured in the production phase for a defined period of time. In one embodiment, the cell culture is contacted with a feed medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the production phase.

A culture produced by the provided methods can be maintained in production phase for between about 1 day and about 30 days. In one embodiment, a culture is maintained in production phase for between about 1 day and about 30 days, between about 1 day and about 25 days, between about 1 day and about 20 days, about 1 day and about 15 days, about 1 day and about 14 days, about 1 day and about 13 days, about 1 day and about 12 days, about 1 day and about 11 days, about 1 day and about 10 days, about 1 day and about 9 days, about 1 day and about 8 days, about 1 day and about 7 days, about 1 day and about 6 days, about 1 day and about 5 days, about 1 day and about 4 days, about 1 day and about 3 days, about 2 days and about 25 days, about 3 days and about 25 days, about 4 days and about 25 days, about 5 days and about 25 days, about 6 days and about 25 days, about 7 days and about 25 days, about 8 days and about 25 days, about 9 days and about 25 days, about 10 days and about 25 days, about 15 days and about 25 days, about 20 days and about 25 days, about 2 days and about 30 days, about 3 days and about 30 days, about 4 days and about 30 days, about 5 days and about 30 days, about 6 days and about 30 days, about 7 days and about 30 days, about 8 days and about 30 days, about 9 days and about 30 days, about 10 days and about 30 days, about 15 days and about 30 days, about 20 days and about 30 days, or about 25 days and about 30 days. In another embodiment, a culture is maintained in production phase for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 15 days, at least about 20 days, at least about 25 days, or at least about 30 days. In a further embodiment, a culture is maintained in production phase for about 1 day, about 2 days, about 3 days, about 4 days, about 5 days, about 6 days, about 7 days, about 8 days, about 9 days, about 10 days, about 11 days, about 12 days, about 15 days, about 20 days, about 25 days, or about 30 days.

The present invention further provides a method of producing a recombinant glycoprotein interest, comprising culturing cells engineered to express the recombinant glycoprotein of interest in a culture comprising a medium described herein; and recovering or isolating the recombinant glycoprotein of interest from the culture. In certain embodiments, the recombinant glycoprotein of interest is an antibody or a fragment thereof. In a specific embodiment, the recombinant glycoprotein of interest is an anti-α4-integrin antibody. In another embodiment, the recombinant glycoprotein of interest is natalizumab.

In a specific embodiment, a method of producing a recombinant glycoprotein of interest according to the present invention produces a maximum glycoprotein titer of at least about 0.05 g/L, at least about 0.1 g/L, at least about 0.25 g/L, at least about 0.5 g/L, at least about 0.75 g/L, at least about 1.0 g/L, at least about 1.5 g/L, at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 8 g/liter, at least about 9 g/liter, or at least about 10 g/liter. In another embodiment, the method according to the present invention produces a maximum glycoprotein titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In a specific embodiment, the glycoprotein is an antibody. In another embodiment, the glycoprotein is a blood clotting factor.

The invention further provides a conditioned cell culture medium produced by a method described herein.

In one embodiment, a conditioned cell culture medium produced according to the provided methods comprises a recombinant glycoprotein of interest. In a specific embodiment, a conditioned cell culture medium according to the invention comprises a recombinant glycoprotein of interest at a titer of at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 8 g/liter, at least about 9 g/liter, or at least about 10 g/liter, or a titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In another embodiment, a conditioned cell culture medium according to the invention comprises a recombinant glycoprotein at a higher titer than the titer obtained without the use of a medium described herein. In a specific embodiment, the protein or polypeptide is an antibody.

Anti-α4-Integrin Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any anti-α4-integrin antibody that can be expressed in a host cell can be used in accordance with the present invention. In one embodiment, the anti-α4-integrin antibody to be expressed is a monoclonal antibody.

Particular anti-α4-integrin antibodies can be made, for example, by preparing and expressing synthetic genes that encode the recited amino acid sequences or by mutating human germline genes to provide a gene that encodes the recited amino acid sequences. Moreover, these antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667, 988; and 5,885,793.

In addition to the use of display libraries, other methods can be used to obtain an antibody. For example, a protein or a peptide thereof can be used as an antigen in a non-human animal, e.g., a rodent, i.e., a mouse, hamster, or rat.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity can be produced and selected. See, e.g., XENOMOUSE™, Green et al. (1994) *Nature Genetics* 7:13-21, U.S. 2003-0070185, WO 96/34096, and WO 96/33735.

In another embodiment, a monoclonal anti-α4-integrin antibody is obtained from the non-human animal, and then modified, e.g., humanized or deimmunized. Winter describes an exemplary CDR-grafting method that can be used to prepare humanized antibodies described herein (U.S. Pat. No. 5,225,539). All or some of the CDRs of a particular human antibody can be replaced with at least a portion of a non-human antibody. In one embodiment, it is only necessary to replace the CDRs required for binding or binding determinants of such CDRs to arrive at a useful humanized antibody that binds to an antigen.

Humanized anti-α4-integrin antibodies can be generated by replacing sequences of the Fv variable region that are not directly involved in antigen binding with equivalent sequences from human Fv variable regions. General methods for generating humanized antibodies are provided by Morrison, S. L. (1985) *Science* 229:1202-1207, by Oi et al. (1986) *BioTechniques* 4:214, and by U.S. Pat. Nos. 5,585, 089; 5,693,761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, can be obtained from a hybridoma producing an antibody against a predetermined target, as described above, from germline immunoglobulin genes, or from synthetic constructs. The recombinant DNA encoding the humanized antibody can then be cloned into an appropriate expression vector. In one embodiment, the expression vector comprises a polynucleotide encoding a glutamine synthetase polypeptide. (See, e.g., Porter et al., *Biotechnol Prog* 26(5):1446-54 (2010).)

The anti-α4-integrin antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies can have mutations in the CH2 region of the heavy chain that reduce or alter effector function, e.g., Fc receptor binding and complement activation. For example, antibodies can have mutations such as those described in U.S. Pat. Nos. 5,624, 821 and 5,648,260. Antibodies can also have mutations that stabilize the disulfide bond between the two heavy chains of an immunoglobulin, such as mutations in the hinge region of IgG4, as disclosed in the art (e.g., Angal et al. (1993) *Mol. Immunol.* 30:105-08). See also, e.g., U.S. 2005-0037000.

In other embodiments, the anti-α4-integrin antibody can be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies can be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit. Rev. Biochem.* 22:259-306. Removal of any carbohydrate moieties present on the antibodies can be accomplished chemically or enzymatically as described in the art (Hakimuddin et al. (1987) *Arch. Biochem. Biophys.* 259:52; Edge et al. (1981) *Anal. Biochem.* 118:131; and Thotakura et al. (1987) *Meth. Enzymol.* 138:350). See, e.g., U.S. Pat. No. 5,869,046 for a modification that increases in vivo half-life by providing a salvage receptor binding epitope.

The anti-α4-integrin antibodies can be in the form of full length antibodies, or in the form of fragments of antibodies, e.g., Fab, F(ab')$_2$, Fd, dAb, and scFv fragments. Additional forms include a protein that includes a single variable domain, e.g., a camel or camelized domain. See, e.g., U.S. 2005-0079574 and Davies et al. (1996) *Protein Eng.* 9(6): 531-7.

In one embodiment, the anti-α4-integrin antibody is an antigen-binding fragment of a full length antibody, e.g., a Fab, F(ab')2, Fv or a single chain Fv fragment. Typically, the anti-α4-integrin antibody is a full length antibody. The anti-α4-integrin antibody can be a monoclonal antibody or a mono-specific antibody.

In another embodiment, the anti-α4-integrin antibody can be a human, humanized, CDR-grafted, chimeric, mutated, affinity matured, deimmunized, synthetic or otherwise in vitro-generated antibody, and combinations thereof.

The heavy and light chains of the anti-α4-integrin antibody can be substantially full-length. The protein can include at least one, and preferably two, complete heavy chains, and at least one, and preferably two, complete light chains or can include an antigen-binding fragment (e.g., a Fab, F(ab')2, Fv or a single chain Fv fragment). In yet other embodiments, the antibody has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody has a light chain constant region chosen from, e.g., kappa or lambda, particularly, kappa (e.g., human kappa).

Cells

Any eukaryotic cell or cell type susceptible to cell culture can be utilized in accordance with the present invention. For example, plant cells, yeast cells, animal cells, insect cells, avian cells or mammalian cells can be utilized in accordance with the present invention. In one embodiment, the eukaryotic cells are capable of expressing a recombinant protein or are capable of producing a recombinant or reassortant virus.

Non-limiting examples of mammalian cells that can be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells ±DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCLS 1); TRI cells (Mather et al., *Annals N.Y. Acad. Sci.,* 383:44-68 (1982)); MRC 5 cells; FS4 cells; and a human hepatoma line (Hep G2). In one embodiment, the present invention is used in the culturing of and expression of polypeptides from CHO cell lines. In a specific embodiment, the CHO cell line is the DG44 CHO cell line. In a specific embodiment, the CHO cell line is the DUXB11 CHO cell line. In a specific embodiment, the CHO cell line comprises a vector comprising a polynucleotide encoding a glutamine synthetase polypeptide. In a further specific embodiment, the CHO cell line expresses an exogenous glutamine synthetase gene. (See, e.g., Porter et al., *Biotechnol Prog* 26(5):1446-54 (2010).)

Additionally, any number of commercially and non-commercially available hybridoma cell lines that express polypeptides or proteins can be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

The eukaryotic cells according to the present invention can be selected or engineered to produce high levels of protein or polypeptide, or to produce large quantities of virus. Often, cells are genetically engineered to produce high levels of protein, for example by introduction of a gene encoding the recombinant glycoprotein of interest and/or by introduction of control elements that regulate expression of the gene (whether endogenous or introduced) encoding the recombinant glycoprotein of interest.

The eukaryotic cells can also be selected or engineered to survive in culture for extended periods of time. For example, the cells can be genetically engineered to express a polypeptide or polypeptides that confer extended survival on the cells. In one embodiment, the eukaryotic cells comprise a transgene encoding the Bcl-2 polypeptide or a variant thereof. See, e.g., U.S. Pat. No. 7,785,880. In a specific embodiment, the cells comprise a polynucleotide encoding the bcl-xL polypeptide. See, e.g., Chiang G G, Sisk W P. 2005. *Biotechnology and Bioengineering* 91(7):779-792.

The eukaryotic cells can also be selected or engineered to modify its posttranslational modification pathways. In one embodiment, the cells are selected or engineered to modify a protein glycolsylation pathway. In a specific embodiment, the cells are selected or engineered to express an aglycosylated protein, e.g., an aglycosylated recombinant antibody. In another specific embodiment, the cells are selected or engineered to express an afucosylated protein, e.g., an afucosylated recombinant antibody.

The eukaryotic cells can also be selected or engineered to allow culturing in serum free medium.

Media

The cell culture of the present invention is prepared in any medium suitable for the particular cell being cultured. In some embodiments, the medium contains e.g., inorganic salts, carbohydrates (e.g., sugars such as glucose, galactose, maltose or fructose), amino acids, vitamins (e.g., B group vitamins (e.g., B12), vitamin A vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), and combinations thereof. Commercially available media such as 5×-concentrated DMEM/F12 (Invitrogen), CD OptiCHO feed (Invitrogen), CD EfficientFeed (Invitrogen), Cell Boost (HyClone), BalanCD CHO Feed (Irvine Scientific), BD Recharge (Becton Dickinson), Cellvento Feed (EMD Millipore), Ex-cell CHOZN Feed (Sigma-Aldrich), CHO Feed Bioreactor Supplement (Sigma-Aldrich), SheffCHO (Kerry), Zap-CHO (Invitria), ActiCHO (PAA/GE Healthcare), Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace, (1979) *Meth. Enz.*, 58:44; Barnes and Sato, (1980) *Anal. Biochem.*, 102:255; U.S. Pat. Nos. 4,767, 704; 4,657,866; 4,927,762; 5,122,469 or 4,560,655; International Publication Nos. WO 90/03430; and WO 87/00195; the disclosures of all of which are incorporated herein by reference, can be used as culture media. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and their suitable carriers, and glucose or an equivalent energy source. In some embodiments the nutrient media is serum-free media, a protein-free media, or a chemically defined media. Any other necessary supplements can also be included at appropriate concentrations that would be known to those skilled in the art.

In one embodiment, the mammalian host cell is a CHO cell and a suitable medium contains a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346-349) with modified concentrations of some components such as amino acids, salts, sugar, and vitamins, recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements. In another embodiment, the suitable medium contains yeast hydrolysate. In a preferred embodiment, the suitable medium contains yeastolate.

The present invention provides a variety of media formulations that, when used in accordance with other culturing steps described herein, minimize or prevent decreases in cellular viability in the culture while retaining the ability to control glycosylation of a recombinant glycoprotein of interest.

A media formulation of the present invention that has been shown to be to useful in manipulating glycosylation, while not having greatly negative impacts on metabolic balance, cell growth and/or viability or on expression of polypeptide or protein comprises the media supplement described herein. One of ordinary skill in the art will understand that the media formulations of the present invention encompass both defined and non-defined media.

Cell Culture Processes

Various methods of preparing mammalian cells for production of proteins or polypeptides by batch and fed-batch culture are well known in the art. A nucleic acid sufficient to achieve expression (typically a vector containing the gene encoding the polypeptide or protein of interest and any operably linked genetic control elements) can be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbentassay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well-known to one of ordinary skill in the art. The cell expressing the polypeptide of interest is typically propagated by growing it at a temperature and in a medium that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The cell density useful in the methods of the present invention can be chosen by one of ordinary skill in the art. In accordance with the present invention, the cell density can be as low as a single cell per culture volume. In some embodiments of the present invention, starting cell densities (seed density) can range from about $2 \times 10^2$ viable cells per mL to about $2 \times 10^3$, $2 \times 10^4$, $2 \times 10^5$, $2 \times 10^6$, $5 \times 10^6$ or $10 \times 10^6$ viable cells per mL and higher.

In accordance with the present invention, a cell culture size can be any volume that is appropriate for production of polypeptides. In one embodiment, the volume of the cell culture is at least 500 liters. In other embodiments, the volume of the production cell culture is 10, 50, 100, 250, 1000, 2000, 2500, 5000, 8000, 10,000, 12,000 liters or more, or any volume in between. For example, a cell culture will be 10 to 5,000 liters, 10 to 10,000 liters, 10 to 15,000 liters, 50 to 5,000 liters, 50 to 10,000 liters, or 50 to 15,000 liters, 100 to 5,000 liters, 100 to 10,000 liters, 100 to 15,000 liters, 500 to 5,000 liters, 500 to 10,000 liters, 500 to 15,000 liters, 1,000 to 5,000 liters, 1,000 to 10,000 liters, or 1,000 to 15,000 liters. Or a cell culture will be between about 500 liters and about 30,000 liters, about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a cell culture will be at least about 500 liters, at least about 1,000 liters, at least about 2,000 liters, at least about 3,000 liters, at least about 5,000 liters, at least about 10,000 liters, at least about 15,000 liters, or at least about 20,000 liters.

One of ordinary skill in the art will be aware of and will be able to choose a suitable culture size for use in practicing the present invention. The production bioreactor for the culture can be constructed of any material that is conducive to cell growth and viability that does not interfere with expression or stability of the produced polypeptide or protein.

The temperature of the cell culture will be selected based primarily on the range of temperatures at which the cell culture remains viable. For example, during the initial growth phase, CHO cells grow well at 37° C. In general, most mammalian cells grow well within a range of about 25° C. to 42° C.

In certain cases, it can be beneficial or necessary to supplement the cell culture during the growth and/or subsequent production phase with nutrients or other medium components that have been depleted or metabolized by the cells. For example, it might be advantageous to supplement the cell culture with nutrients or other medium components observed to have been depleted. Alternatively or additionally, it can be beneficial or necessary to supplement the cell culture prior to the subsequent production phase. As non-limiting examples, it can be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components, including the amino acids, can all be added to the cell culture at one time, or they can be provided to the cell culture in a series of additions. In one embodiment of the present invention, the supplementary components are provided to the cell culture at multiple times in proportional amounts. In another embodiment, it can be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture can be 1, 2, 3, 4, 5, 6, 7, 8, 9, 10, 15, 20, 25, 30, 35, 40, 45 or 50% of the volume of the cell culture prior to providing the supplementary components.

The cell culture can be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base and oxygenation can be controlled with sparging devices that are well known in the art.

In certain embodiments of the present invention, the practitioner can find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase.

In order to monitor certain cell culture conditions, it will be necessary to remove small aliquots of the culture for analysis. One of ordinary skill in the art will understand that such removal can potentially introduce contamination into the cell culture, and will take appropriate care to minimize the risk of such contamination.

As non-limiting example, it can be beneficial or necessary to monitor temperature, pH, cell density, cell viability, integrated viable cell density, lactate levels, ammonium levels, osmolarity, or titer of the expressed polypeptide or protein. Numerous techniques are well known in the art that will allow one of ordinary skill in the art to measure these conditions. For example, cell density can be measured using a hemacytometer, a Coulter counter, or Cell density examination (CEDEX). Viable cell density can be determined by staining a culture sample with Trypan blue. Since only dead cells take up the Trypan blue, viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as coomassie staining of SDS-PAGE gels, Western blotting, Bradford assays, Lowry assays, Biuret assays, and UV absorbance. It can also be beneficial or necessary to monitor the post-translational modifications of the expressed polypeptide or protein, including phosphorylation and glycosylation.

The practitioner can also monitor the metabolic status of the cell culture, for example, by monitoring the glucose, lactate, ammonium, and amino acid concentrations in the cell culture, as well as by monitoring the oxygen production or carbon dioxide production of the cell culture. For example, cell culture conditions can be analyzed by using NOVA Bioprofile 100 or 400 (NOVA Biomedical, Wash.). Additionally, the practitioner can monitor the metabolic state of the cell culture by monitoring the activity of mitochondria. In one embodiment, mitochondrial activity can be monitored by monitoring the mitochondrial membrane potential using Rhodamine 123. Johnson L V, Walsh M L, Chen L B. 1980. *Proceedings of the National Academy of Sciences* 77(2):990-994.

Isolation of Expressed Polypeptide

In general, it will typically be desirable to isolate and/or purify proteins or polypeptides expressed according to the present invention. In one embodiment, the expressed polypeptide or protein is secreted into the medium and thus cells and other solids can be removed, as by centrifugation or filtering for example, as a first step in the purification process.

Alternatively, the expressed polypeptide can be bound to the surface of the host cell. In this embodiment, the media is removed and the host cells expressing the polypeptide or protein are lysed as a first step in the purification process. Lysis of mammalian host cells can be achieved by any number of means well known to those of ordinary skill in the art, including physical disruption by glass beads and exposure to high pH conditions.

The polypeptide can be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein can be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin can be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

Pharmaceutical Compositions

A polypeptide can be formulated as a pharmaceutical composition for administration to a subject, e.g., to treat or prevent a disorder or disease. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (See e.g., Berge, S. M., et al. (1977) *J. Pharm. Sci.* 66:1-19). In one embodiment, a pharmaceutical composition is an immunogenic composition comprising a virus produced in accordance with methods described herein.

Pharmaceutical formulation is a well-established art, and is further described, e.g., in Gennaro (ed.), Remington. The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

The pharmaceutical compositions can be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically compositions for the agents described herein are in the form of injectable or infusible solutions.

In one embodiment, the antibody is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the polypeptide can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

The foregoing description is to be understood as being representative only and is not intended to be limiting. Alternative methods and materials for implementing the invention and also additional applications will be apparent to one of skill in the art, and are intended to be included within the accompanying claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis*, M. J. Gait ed., (1984); Mullis et al. U.S. Pat. No: 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in Antibody Engineering, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical-Immunology* (8th ed.), Appleton & Lange, Norwalk, Conn. (1994) and Mishell and Shiigi (eds), *Selected Methods in Cellular Immunology*, W. H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunology* $4^{th}$ ed. Ed. Richard A. Goldsby, Thomas J. Kindt and Barbara A. Osborne, H. Freemand & Co. (2000); Roitt, I., Brostoff, J. and Male D., Immunology 6th ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, Genes VIII, Prentice Hall (2003); Harlow and Lane, *Antibodies: A Laboratory Manual*, Cold Spring Harbor Press (1988); Dieffenbach and Dveksler, PCR Primer Cold Spring Harbor Press (2003).

All of the references cited above, as well as all references cited herein, are incorporated herein by reference in their entireties.

EXAMPLES

During the natalizumab $2^{nd}$ Generation ("T2G") manufacturing process, variability in drug substance pI isoforms and % Galactosylation ("Gal") was observed. As shown in FIG. 1, % Gal values trended high and were close to the upper specification limit of 31.8% for several batches. An analysis of the 11 charge variant peaks of the antibody showed that Peak 5 exhibited the most variation and was likely driving the shifts in the relative levels of the other charge variant peaks. Furthermore, % Gal was observed to trend inversely proportional with % Peak 5 (FIG. 1), making it a peak of interest for predicting Gal values.

Observed and predicted values for the pool peak isoforms of the antibody in MFM-133-12-R060 were compared (FIG. 2). The modeling showed that variation in Peak 5 content was very well described by cell culture in-process data, particularly by lactate and pH values from the production bioreactor.

In the T2G manufacturing process, the production bioreactor pH was controlled at 7.0±0.2 through the addition of $CO_2$ (upper deadband) and $Na_2CO_3$ (lower deadband). Culture pH, which is directly impacted by cell net lactate production, drifted between the upper and lower control limits through the production run. As demonstrated through modeling, large-scale manufacturing (LSM) trends showed that an increase in Peak 5/decrease in Gal levels could be correlated to a decrease in cell lactate production/increase in Day 8 culture pH (FIGS. 3A-3D).

Based on this understanding, small-scale studies were carried out to identify implementable methods for controlling product quality, specifically Peak 5 and Gal levels. The methods tested aimed to modulate lactate and pH levels in the production culture. Studies were also carried out concurrently to identify sources of the observed product quality variability, particularly relating to TC yeastolate lot-to-lot variation. It was found that copper addition is an effective approach for controlling Peak 5 and Gal levels. Further, it was demonstrated that copper variation in yeastolate is a significant source of product quality variability through analytical testing and supporting laboratory results.

Example 1

Effect of Copper (II) Sulfate on Cell Culture

The impact of different copper levels in the culture on cell metabolism and Peak 5/Gal was evaluated in shake flask studies. In four separate experiments, varying amounts of copper (II) sulfate was added to the production culture on Day 0 and cells were cultured under different $CO_2$ conditions. FIG. 4A shows a plot of % Peak 5 against Day 8 pH with copper addition. FIG. 4B shows a plot of % Gal against Day 8 pH with copper addition. Day 8 pH was chosen as a time point primarily because it is a good marker of the lactate metabolism of the culture.

Cell net lactate production decreased as copper was added to the culture. Since culture pH is directly driven by lactate production, an increase in pH was observed. Increase in pH levels due to copper addition correlated with an increase in % Peak 5 ($R^2=0.95$) and decrease in % Gal ($R^2=0.91$). The correlation found in the small-scale experiments also aligned well with data gathered from large-scale manufacturing as shown in FIGS. 4A and 4B.

Example 2

Trace Copper Concentrations in Yeastolate

An analysis of LSM data showed that within a single lot of TC yeastolate used for two batches (I08864), consistent viable cell density, pH and lactate concentration profiles were observed (TR-MS-000030). Using X-Ray Fluorescence (XRF) and ICP-MS, trace metal concentrations present in 20 yeastolate lots were also measured.

In XRF, X-ray photons of sufficient energy strike an atom and dislodge an electron from one of the inner electron orbitals, typically the K and/or L shell. To regain stability, an electron from one of the outer orbitals fills this vacancy and, in the process, excess energy is released in the form of an X-ray photon. Because the quantum states of each atom's electrons are fairly unique, the energy of the emitted photons are characteristic of the elements present and the number of photons detected at a specific energy is proportional to the concentration of that element in the sample. Palmer, P. T. et al., *J. Agr. Food Chem.* 57(7):2605-2613 (2009).

ICP-MS (inductively coupled plasma mass spectrometry) is a type of mass spectrometry. ICP-MS mostly utilizes noble gases, such as argon as plasma gas, in which the efficient vaporization, dissociation or atomization, excitation, and final ionization of the sample constituents to be analyzed takes place. In addition, this high temperature process leads to a complete fragmentation of every sample molecule, leaving only their detectable, atomic constituents, which could then be used as surrogates to also detect complex molecules. Pröfrock, D. and Prange, A., *Appl. Spectr.* 66(8):843-868 (2012).

Copper concentrations were found to vary from approximately 0.6 to 2.3 ppm among the different yeastolate lots. Strong correlations ($R^2$>0.58) were observed between the measured copper levels in yeastolate to LSM cell culture lactate/pH levels and Peak 5/Gal levels, as shown in FIGS. 5A-5D.

Example 3

Other Sources of Trace Copper Contamination

Trace copper contamination was measured and detected in most of the other raw materials used in the T2G manufacturing process, but at very low levels. An initial screen on a wide set of raw materials (NMB1, IMF2.0v3, Sodium Bicarbonate, L-Tyrosine, Tropolone, Ammonium Ferric Citrate Brown, HEPES, D-Glucose, Gibco Cholesterol Lipid Concentrate) was performed by XRF. Raw materials (IMF and Sodium Bicarbonate) which showed significant copper levels were submitted for ICP-MS analysis to quantify concentrations. Table 1 highlights the copper levels in two lots of IMF2.0v3 and $NaHCO_3$ powder, and their corresponding concentrations in the media, feed, and culture; the two lots shown for each raw material each had the highest and lowest copper concentrations out of 6 to 8 lots measured. Copper concentrations from yeastolate were also listed for comparison. It should be noted that the IMF formulation had a target copper concentration of 80 nM, which accounts for 73.3 nM of the copper measured in the prepared nutrient feed.

TABLE 1

| Raw Material | Copper Concentration in powder, measured by ICP-MS (ppm) | Calculated Copper Concentration | | | |
|---|---|---|---|---|---|
| | | Media (nM) | Nutrient Feed (nM) | Day 0 Culture (nM) | Day 9 Culture (nM) |
| Yeastolate | | | | | |
| R08543 | 0.675 | 13.3 | 607.4 | 13.3 | 98.3 |
| R08216 | 2.251 | 44.3 | 2025.5 | 44.3 | 327.9 |
| IMF2.0v3 | | | | | |
| R09573 | 0.09 | — | 134.9 | 0 | 18.9 |
| R08496 | 0.14 | — | 209.9 | 0 | 29.4 |
| $NaHCO_3$ | | | | | |
| R08658 | 0.02 | 0.73 | — | 0.73 | 0.73 |
| C41485 | 0.05 | 1.81 | — | 1.81 | 1.81 |

The reported data provided a magnitude of the contribution of each raw material to additional copper in the culture, and of the copper variation among different lots. It was observed that trace copper contamination originating from IMF2.0v3 and $NaHCO_3$ were very low when compared to that from yeastolate.

Media and nutrient feed retains were also sent for external ICP-MS testing to evaluate other potential sources of copper contamination and consistency in the copper levels between Facilities A and B. Copper levels were below the limit of detection in the media samples. FIG. 6 shows the copper concentration measured in the nutrient feed for 3 Facility A and Facility B batches using the same yeastolate lot. The measured copper levels were compared to the calculated levels based on measurements in the yeastolate powder.

No considerable differences were observed between sites or between the measured and calculated copper concentrations in the nutrient feed samples, demonstrating that yeastolate powder was the main source of copper contamination.

Example 4

Copper Supplementation to Yeastolate

Based on the XRF copper concentration measurements, the effects of copper supplementation to low-copper yesatolate lots on cell metabolism and Peak 5/Gal levels were evaluated in 1 L production shake flask cultures. Yeastolate lots with 0.675 ppm (R08543) and 2.251 ppm (R08216) of measured copper concentrations were chosen. TC yeastolate R08543 was supplemented with 1.576 ppm of additional copper (II) sulfate to match the amount of copper present in TC yeastolate R08216, and the impact of copper supplementation on cell growth, lactate, and pH are shown in FIGS. 7A-7C. The T2G culture media is made with 1.25 g/kg of yeastolate while the IMF nutrient, which is fed to cultures from days 3 to 11 at 2% volume, is made with 57.14 g/kg of yeastolate.

Significant differences were observed in cell metabolism and growth profiles with cultures receiving yeastolates from the two different lots. Copper supplementation to TC yeastolate R08543 signficantly reduced lactate production, increased culture pH, and recovered the cell growth performance of the cultures in a manner similar to those receiving TC yeastolate R08216. With copper supplementation, Peak 5 levels increased from an average of 8.2 to 13.4% and Gal levels decreased from an average of 25 to 15%, to match those of Lot R08216 cultures (FIGS. 8A and 8B).

The same experiment was also carried out with yeast extracts from Bio Springer. Becton Dickinson (BD), which is the primary supplier of the TC yeastolate used in the T2G process. BD acquires yeast extract from Bio Springer and adds proprietary supplements to the yeast extracts before supplying them for use. Using XRF, copper concentrations in two lots of yeast extracts were measured to be 0.519 ppm (Lot 1) and 1.084 ppm Lot 2. Lot 1 was supplemented with 0.57 ppm of additional copper (II) sulfate to match the amount of copper present in Lot 2 (Lot 1+2× Cu).

As shown in FIGS. 9A-9C, copper supplementation reduced lactate levels and caused an increase in both pH and growth in Lot 1+2× Cu cultures to match the profiles of Lot 2 very closely.

Similarly, an increase in Peak 5 levels from an average of 8.1 to 9.1% and a decrease in Gal levels from an average of 25 to 19.1% was observed when copper was added to Lot 1 (FIGS. 10A and 10B). The different copper levels measured in Bio Springer yeast extracts also indicate that the variation of this metal concentration is inherent to the non-chemically defined nature of the raw material.

Example 5

Methods for Controlling Cell Culture

Evidence through both large-scale data and small-scale studies suggested that the variation in copper levels among yeastolate lots is a significant source of the observed product quality variability, and that controlling copper levels within yeastolate would be an effective method of modulating product quality.

A stress test was carried out with copper addition to yeastolate at high concentrations to identify risks and failure points. In two separate experiments, copper (II) sulfate was added at different concentrations up to 6× and 10× copper in TC yeastolate R08543 (Control), respectively:

TABLE 2

| Experiment 1 | | Experiment 2 | |
| --- | --- | --- | --- |
| Group | Cu in TC yeastolate (ppm) | Group | Cu in TC yeastolate (ppm) |
| Control | 0.68 | Control | 0.68 |
| 2.2X Cu | 1.46 | 3.3X Cu | 2.25 |
| 3.3X Cu | 2.25 | 6X Cu | 4.05 |
| 5X Cu | 3.38 | 8X Cu | 5.40 |
| 6X Cu | 4.05 | 10X Cu | 6.75 |

In Experiment 1, no negative impact on cell growth and titer were observed up to 4.05 ppm Cu in yeastolate (FIG. 11A). In Experiment 2, the highest cell growth was observed at 3.3× Cu, with peak viable cell density (VCD) reaching approximately 1.2E+07 vc/mL. A decline in the cell growth profile was observed as copper concentrations increased to 8× and 10× Cu; nevertheless, the profiles were still comparable to that of the control group (FIG. 11B). There was no significant differences in titer among all groups. The concentration of copper in yeastolate measured was no higher than 2.25 ppm while the experimentally tested copper concentration was up to 6.75 ppm. This study demonstrated that no negative growth or titer impact of copper would be expected when copper was added to the yeastolate at the studied levels.

FIG. 12 shows the impact of high copper concentrations on Peak 5 and Peak 4. At large-scale, harvest material was processed over the TMAE column which reduces Peak 5 (average 2.9%) while enriching Peak 4 (average 6.9%). As laboratory samples were purified through a single Protein A column, results were adjusted to account for Peak 5 reduction/Peak 4 enrichment for a better comparison to LSM data.

While there is no specification limit for Peak 5, both LSM and experimental data showed that increases in this peak content also drove a decrease in % Peak 4 towards its lower specification limit of 58.4%. Projection of this data set showed that at approximately 4 ppm Cu, Peak 4 hits its lower limit, thereby placing a limit on Peak 5 at 15%. Increases in Peak 5 content at high copper concentrations also reduces % Gal, which has a lower specification limit of 13.4% (FIG. 13).

Experimental data showed that for the copper concentrations tested, Gal levels were never driven below the specification; minimal changes in Gal levels were observed above 3.5 ppm Cu. At 4 ppm Cu and the projected Peak 5 limit of 15%, Gal decreased to approximately 15%.

Example 6

Copper Operating Range for Cell Culture

The highlighted region in FIG. 14 was proposed as the target copper operating range. Stress tests indicated that a negative impact on growth or failure due to Peak 5/Peak 4 may occur above 4 ppm Cu in yeastolate. The proposed range remains with the range of variation and is significantly below the failure point.

To arrive at this operating range, it was proposed that TC yeastolate lots be supplemented with copper when needed. An acceptable range of copper concentration in yeastolate would be provided. It would be required that the copper concentration of each incoming lot of yeast extract would be measured through ICP-MS or XRF. All TC yeastolate lots with copper levels within the range provided would be accepted. For lots with copper levels below the acceptable range, it would be required that those lots be supplemented with copper (II) sulfate up to a target concentration, the lots be retested, and the final concentrations reported. Lots with copper levels above the controlled range would not be used. This method would allow for a tighter control of the raw material over an operating range that remains within experience.

Example 7

Additional Experiments Studying the Impact of Copper on T2G Product Quality

Experiments were carried out in 1 L shake flasks and levels of copper in yeastolate were manipulated to be between 0.6 ppm and 6.8 ppm. All LSM values were drug substance data while laboratory samples were purified through a single Protein A column. FIGS. 15A and 15B show no impact of increasing copper levels on % aggregate and % half antibody.

FIGS. 16A-16J shows plots of acidic and basic pI isoforms against copper concentration. Copper had no impact on acidic isoforms (Peaks 1 to 3). With the exception of Peaks 7 and 11, copper was observed to impact all other basic isoforms.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

What is claimed is:

1. A method for achieving a predetermined galactosylation profile of an anti-α4-integrin antibody comprising:
    culturing host cells producing the anti-α4-integrin antibody in a cell culture comprising an amount of copper within a target copper concentration range, wherein the target copper concentration range in the cell culture is between 200 nM and 500 nM, wherein the target copper concentration is achieved by supplementing the cell culture with a yeast hydrolysate comprising copper.

2. The method of claim 1, comprising supplementing the cell culture with the yeast hydrolysate comprising copper if the copper concentration in the cell culture is below the target copper concentration range.

3. The method of claim 1, wherein the target copper concentration is maintained through a feedback loop.

4. The method of claim 1, wherein the copper concentration is constantly monitored and maintained within the target copper concentration range.

5. The method of claim 1, wherein the target copper concentration is achieved with a single dose of the yeast hydrolysate comprising copper.

6. The method of claim 1, wherein the anti-α4-integrin antibody is produced by a eukaryotic host cell.

7. The method of claim 6, wherein the eukaryotic host cell is a mammalian host cell.

8. The method of claim 1, wherein the copper concentration alters the levels of the isoform variants of the anti-α4-integrin antibody.

9. The method of claim 1, wherein the anti-α4-integrin antibody is natalizumab.

10. The method of claim 1, wherein the yeast hydrolysate used to supplement the cell culture comprises copper (II) sulfate.

11. The method of claim 1, wherein the target copper concentration range in the cell culture is transitioned to between 200 nM and 500 nM after an initial culture comprising a target copper concentration of between 20 nM and 50 nM.

* * * * *